United States Patent
Walker et al.

[11] Patent Number: 6,041,252
[45] Date of Patent: *Mar. 21, 2000

[54] DRUG DELIVERY SYSTEM AND METHOD

[75] Inventors: Jeffrey P. Walker, San Diego; Robert M. Bernard, Rancho Santa Fe, both of Calif.

[73] Assignee: Ichor Medical Systems Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/476,714

[22] Filed: Jun. 7, 1995

[51] Int. Cl.$^7$ ....................................................... A61N 1/30
[52] U.S. Cl. ......................... 604/20; 604/21; 435/173.6; 435/285.2; 607/72
[58] Field of Search .................................. 604/20–21, 49; 935/52–53; 435/173.6, 285.2; 607/72

[56] References Cited

U.S. PATENT DOCUMENTS

| | | |
|---|---|---|
| 5,389,069 | 2/1995 | Weaver . |
| 5,439,440 | 8/1995 | Hofmann . |
| 5,462,520 | 10/1995 | Hofmann . |
| 5,464,386 | 11/1995 | Hofmann . |
| 5,472,441 | 12/1995 | Edwards et al. . |
| 5,501,662 | 3/1996 | Hofmann . |
| 5,507,724 | 4/1996 | Hofmann . |
| 5,545,130 | 8/1996 | Hofmann . |
| 5,547,467 | 8/1996 | Pliquett . |
| 5,667,491 | 9/1997 | Pliquett . |
| 5,674,267 | 10/1997 | Mir et al. . |
| 5,676,646 | 10/1997 | Hofmann . |
| 5,688,233 | 11/1997 | Hofmann . |
| 5,702,359 | 12/1997 | Hofmann . |
| 5,704,908 | 1/1998 | Hofmann . |
| 5,749,847 | 5/1998 | Zewert . |

*Primary Examiner*—Mark Bockelman
*Attorney, Agent, or Firm*—James C. Weseman, Esq.; The Law Offices of James C. Weseman

[57] ABSTRACT

A method for delivering a therapeutic agent to a predetermined location in a host is disclosed, wherein a liposome-encapsulated therapeutic agent is administered to the host, and an electrical field which encompasses a predetermined region in the host is established, such that as the liposome-encapsulated agent is exposed to the electrical field the release of the agent from the liposome to the predetermined region is enhanced.

12 Claims, 2 Drawing Sheets

DRUG DELIVERY SYSTEM AND METHOD

TECHNICAL FIELD

This invention relates generally to the delivery of therapeutic agents to specific locations in patients, and, more particularly, to effecting such delivery by utilizing electrical fields to localize the delivery of such agents within the patient.

BACKGROUND OF THE INVENTION

Numerous medical therapies have attempted to treat localized disease in the body of a patient with techniques designed to direct the appropriate drug to the affected area and to avoid unacceptable or toxic side effects to healthy tissue. For example, therapies have been proposed utilizing liposomes as vehicles to carry the appropriate drugs to the diseased area.

Liposomes are microscopic particles which are made up of one or more lipid bilayers enclosing an internal compartment. They are not normally leaky but can become leaky if a hole or pore occurs in the membrane, if the membrane is dissolved or degrades, or if the membrane temperature is increased to the transition temperature, $T_C$. The major barrier to the use of liposomes as drug carriers is making the liposome release the drugs on demand at the target sites (*Science* 202:1290 (1978)).

The specific use of applied heat to raise the liposome temperature to $T_C$ to make them leaky or permeable has been described (*Science* 204:188 (1979)). This technique has been proposed in U.S. Pat. No. 5,190,761 in which a method of activating liposomes to release their encapsulated drugs in tissue utilizing microwave radiation is described.

Additionally, it has been proposed that electroporation can be used to deliver what are normally non-permeable substances into the interior of tumor cells, thus affecting changes on an intracellular basis. Attempts to perform this delivery have only recently been successful (Ceberg et al. (1994)). One difficulty has been the confinement of the electroporation effect to the desired area. Widespread electroporation effects have been described in which not only the diseased area but also normal contralateral and normal ipsilateral brain†tissue have been affected (Salford et al. (1993)).

The currently available methods of electroporation drug delivery as described in the literature fall short of providing an effective methodology, due primarily to the inability to limit the scope of the electroporation effect to the intended target tissue. Under these circumstances, an unacceptably high level of normal tissue effect is noted and offsets the potential useful benefits of electroporation treatment.

In particular, there are a number of applications in tumor therapy, such as the treatment of glioblastoma multiforme tumors, which would benefit from a treatment methodology in which the delivery of a therapeutic agent is highly localized. At the present time, there is no cure for this uniformly fatal brain tumor which kills over 7,000 U.S. citizens each year.

Therefore, it would be desirable to have available an effective system or methodology which combines the advantage of selective drug delivery using a combination of techniques including electroporation in order to deliver drugs to selected diseased areas.

DESCRIPTION OF THE PRIOR ART

General references of interest regarding electroporation include, for example, *Guide to Electroporation and Electrofusion*, D. C. Chang et al., Eds., Academic Press, Inc, San Diego, Calif. (1992) and *Electroporation and Electrofusion in Cell Biology*, (E. Neumann et al., Eds., Plenum Press, N.Y. (1982).

*Biochemical and Biophysical Research Communications*, 194(No. 2): 938 (1993) discusses a new brain tumor treatment combining bleomycin with in vivo electroporation. A similar article which is currently in press, *Anti-Cancer Drugs* 5:463 (1994) also relates techniques of in vivo electroporation for the purpose of delivering enhanced boron uptake in gliomas to improve boron neutron capture therapy.

References pertaining to surfactant treatment of damaged cell membranes are found in *Annals New York Academy of Sciences* 720:239 (1994) and in *Proc. Natl. Acad. Sci. USA*. 89:4525–28 (1992).

Intermittent hypothermic asanguineous cerebral perfusion (cerebroplegia) is discussed in *J. Thorac. Cardiovasc. Surg.* 99:878 (1990) and further in *J. Thorac. Cardiovasc. Surg.* 102:85 (1991).

General references of interest regarding liposomes include, for example, *Liposome Technology*, Volumes I, II and III, G. Gregoriadis, Ed., CRC Press, Inc., Boca Raton, Fla. (1985) and *Radiation Research* 103:266 (1985).

*Biochim. Biophys. Acta* 150:333 (1968), discloses the use of cholesterol to produce a solid phase liposome. *Biochim. Biophys. Acta* 164:509 (1977) discloses the effect of cholesterol incorporation on the temperature dependence of water permeation through liposome membranes prepared from phosphatidylcholine.

Resealing of electropores is discussed in *Proc. Natl. Acad. Sci. USA* 89:4524 (1992) and also in *Annal. New York Acad. Sci.* (1992).

*Radiation Research* 122:161 (1990) and references therein, disclose the use of heat from a waterbath to release drugs from liposomes that possess a phase transition temperature ($T_C$).

DISCLOSURE OF THE INVENTION

The present invention provides a system and method for the localized delivery of therapeutic agents to patients in need of such treatment. The invention utilizes a number of aspects which can be practiced in a variety of combinations to effect such localized delivery. Such aspects include electropermeabilization, liposome-mediated drug delivery, localized tissue temperature control, three-dimensional electrode arrays and convection enhancement of therapeutic agent concentrations.

In one aspect, the present invention provides a method for delivering a therapeutic agent to a predetermined location in a host. The method comprises providing a liposome-encapsulated therapeutic agent to the host, establishing an electrical field which encompasses a predetermined region within the host, and exposing the liposome-encapsulated agent to the electrical field so as to enhance the release of the agent from the liposome to the predetermined region.

In the practice of such aspects of the present invention the release of the contents of both solid and fluid liposomes is greatly increased by exposure to high voltage transient electrical fields. It has been shown (Mueller et al. (1983) and Chang et al. (1992)) that liposomes exposed to brief external high voltage electrical fields have demonstrated the formation of pores and, above a critical voltage ($E_C$), the liposomes will rupture. These effects can occur either at normal body temperature, over a wide range of temperatures, or through non-thermal interaction with non-ionizing electromagnetic radiation at temperatures other than $T_C$. Thus, the present invention offers a fast and effective method for rapid release of liposome encapsulated therapeutic agents and/or other chemicals into localized areas in cells, tissues, or organs in the body of a patient.

In accordance with certain aspects of the invention, liposomes may be made of inexpensive materials and the drug release from these liposomes can be effected by applying to the predetermined treatment area an electrical field of intensity sufficient to effect the release of the drug from the liposomes.

In certain embodiments, the present electroporation effects are delivered in a manner which utilizes an electrode array which comprises both central and satellite electrodes located in and around, e.g, tumoral or diseased tissue.

More specifically, aspects of the present invention relate to the use of liposomes to deliver drugs or other chemicals to specific target cells or groups of cells such that the drug or chemical is released into the target cells (using electroporation and other techniques) while minimizing entry of said chemicals or drugs into normal healthy cells. The liposome vesicles are designed to be employed at temperatures slightly below their phase transition temperature ($T_C$).

In additional aspects of the invention, techniques will be employed to "precondition" the tumor or diseased tissue, in order to increase the permeabilization effects of the electroporation pulses.

Additionally, techniques designed specifically to protect the normal tissue from the effects of electroporation pulses are provided in certain aspects of the invention, including techniques such as cerebroplegia, which allows the brain to be cooled to subthreshold electroporation and low metabolic activity states. Cerebroplegia provides a second protective mechanism to normal tissue; removal of the therapeutic agent from normal tissue prior to electroporation. These techniques will also be employed to protect healthy tissue from the effect of the electroporation fields, resulting in a more specific loading of the target tissue with drugs or chemicals.

Further, aspects of the invention provide the ability to influence the concentration of administered therapeutic agents via iontophoretic field application which will influence charged liposomes and promote adsorption to cell membranes, as well as influence distribution within diseased tissue.

The present invention will also promote rapid healing of the electropores utilizing surfactant materials which can be delivered to the sites of electroporation via either vascular methods or via liposomes.

DETAILED DESCRIPTION OF THE INVENTION

Figure 1:
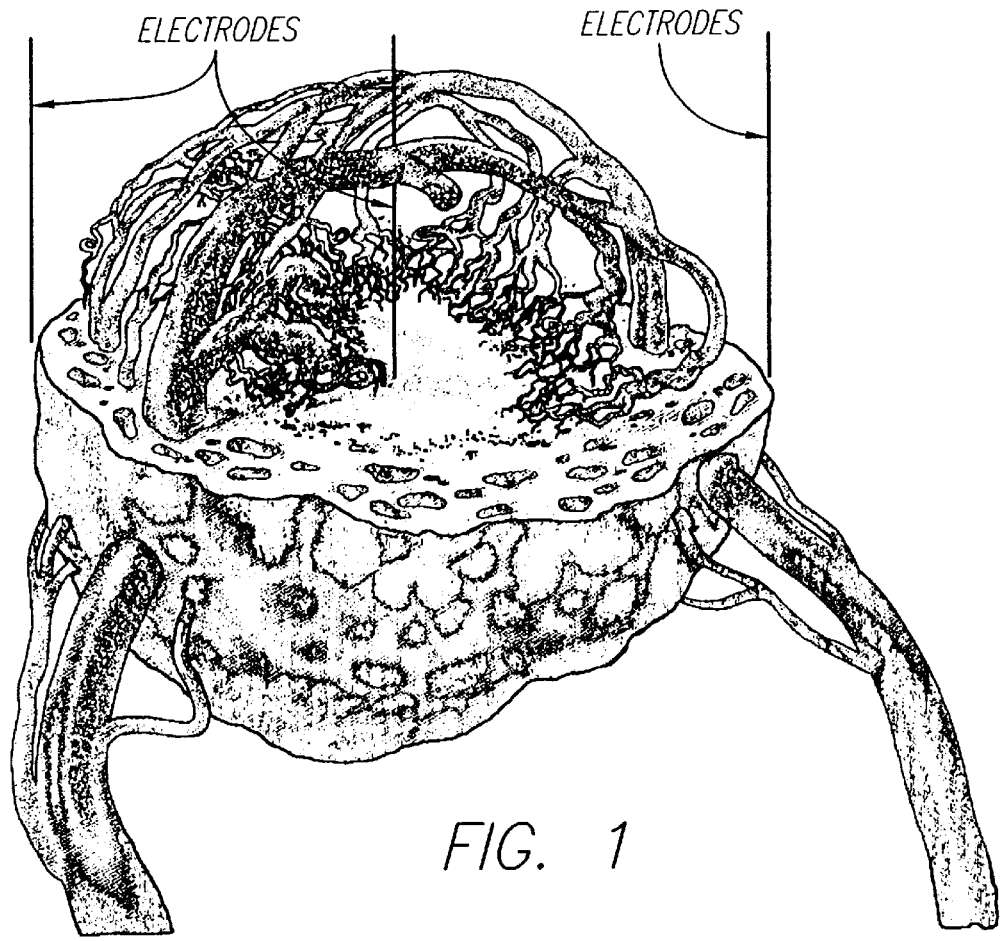
FIG. 1 is a graphic representation illustrating an electrode array in accordance with the invention which is positioned into and around a brain tumor.
Figure 2:
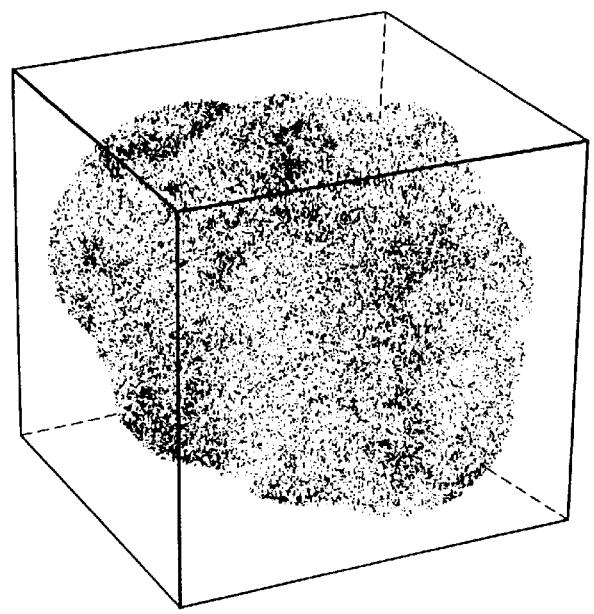
FIG. 2 is a graphic representation of a brain tumor in three-dimensional space.
Figure 3:
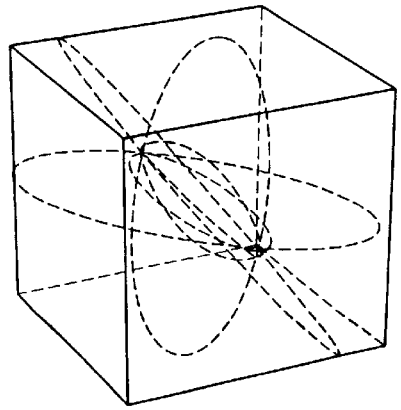
FIG. 3 is a graphic representation of the electrical field lines produced by a bipolar electrode array, wherein the field density is represented by the space between the field lines, with a higher intensity represented by closely spaced field lines, as seen in the region directly between the two electrodes. The application of an electropermeabilization pulse between these two electrodes will ordinarily provide subthreshold electrical pulses to large areas of the tumor (widely-spaced lines) thus reducing the effectiveness of the permeabilization in those areas.
Figure 4:
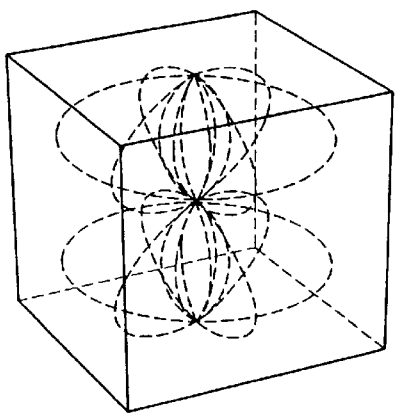
FIG. 4 is a graphic representation of the electrical field lines produced by a three electrode array, with the satellite electrodes placed superior and inferior to the tumor mass.
Figure 5:
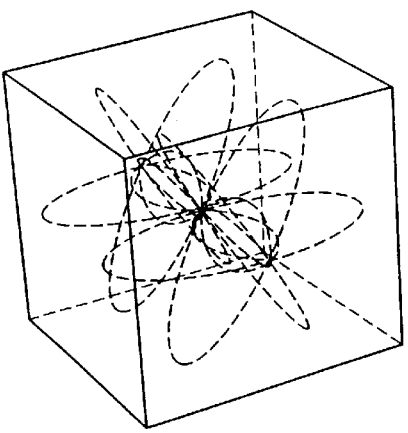
FIG. 5 is a graphic representation of the electrical field lines produced by a three electrode array, with the satellite electrodes placed anterior and posterior to the tumor mass, generally as depicted in FIG. 1. As will be seen, due to the higher density of electrical field lines in the central portion of the tumor (tightly-spaced field lines), the application of an electropermeabilization pulse in this electrode array (as in the array of FIG. 4) will provide above threshold electrical pulses to large areas of the tumor, and subthreshold pulses to the healthy tissue surrounding the tumor, thus increasing the effectiveness of the permeabilization in the tumor.
Figure 6:
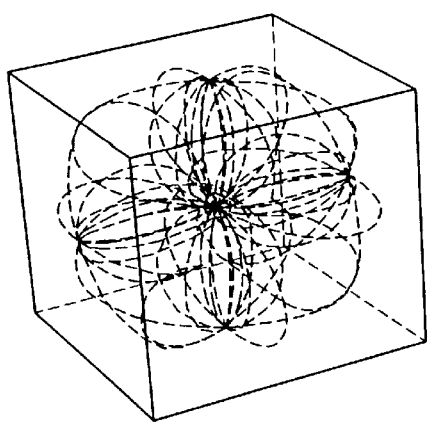
FIG. 6 is a graphic representation of the electrical field lines produced by a five electrode array, with the satellite electrodes placed anterior, posterior, superior and inferior to the tumor mass. As with the array of FIGS. 4 and 5, the effectiveness of the permeabilization in the tumor will be further enhanced with this more complex electrode array.

The present invention provides for the localized delivery of therapeutic agents to patients in need of such treatment. The invention utilizes a number of aspects which can be practiced in a variety of combinations to effect such localized delivery.

In one aspect, the present invention provides a method for delivering a therapeutic agent to a predetermined location in a host. The method comprises providing a liposome-encapsulated therapeutic agent to the host, establishing an electrical field which encompasses a predetermined region within the host, and exposing the liposome-encapsulated agent to the electrical field so as to enhance the release of the agent from the liposome to the predetermined region.

As used herein:

The term "electroporation" refers to a phenomenon wherein the membrane of a cell exposed to high-intensity electrical field pulses can be temporarily destabilized, resulting in increased permeability to exogenous molecules across portions of the membrane.

The term "electropermeabilization" refers more generally to the phenomenon of increased permeability following in vivo electroporation pulses without requiring the formation of physical pores in the membrane.

The terms "drug" and "therapeutic agent" are used interchangeably to refer to any agent which has a desirable pharmacological action when administered to a patient.

The term "liposome" refers to a bilayer structure comprised of a natural or synthetic phospholipid membrane or membranes, and optionally other membrane components such as cholesterol and protein, which structure can act as a physical reservoir for drugs. These drugs may be sequestered in the liposome membrane or may be encapsulated in the aqueous interior of the vesicle. Liposomes are generally characterized according to size and to number of membrane bilayers. The vesicle diameter can be large (>200 nm) or small (<50 nm) and the bilayer can have a unilamellar, oligolamellar, or multilamellar membrane.

The term "phase transition temperature ($T_C$)" refers to the temperature at which a liposome membrane displays both phase states, i.e., fluid (liquid) and solid (gel), simultaneously. The fluid (liquid ) state is characterized by free rotational motion within the membrane of the hydrocarbon chains of the phospholipids, whereas the solid (gel) state is associated with restricted hydrocarbon tail motion. At $T_C$ both phase states coexist and the liposome membrane becomes naturally permeable or leaky, resulting in the spontaneous release of encapsulated drug from the liposome membrane or from the interior space of the liposome. At temperatures below $T_C$ the bilayer is referred to as being in the solid or gel state, and at temperatures above $T_C$ the bilayer is in a liquid or fluid state. To have a phase transition in the liposome bilayer generally requires the exclusive presence of highly purified phospholipids of identical fatty acid chain length and polar head group composition. Mixing phospholipid species or adding perturbing agents at appropriate concentrations will obliterate the ability of the bilayer to undergo a phase transition.

The term "perturbing agent" refers to a natural or synthetic compound or a combination of compounds which when added to a liposome membrane obstructs the formation of a phase transition. The amount of perturbing agent necessary to obstruct the formation of a phase transition varies according to the stearic nature of the compound. Usually, but not always, 20–40 percent mole fraction of the agent is required. Typically a perturbing agent is selected from natural or synthetic compounds: cholesterol; phospholipids, for example egg phosphatidylcholine (EPC) or lecithin, egg phosphatidylglycerol (EPG); inorganic metal compounds and complexes and proteins such as antibodies. Perturbing agents also include various compositions of phosphatidylcholine or phosphatidylglycerol, or phosphatidylethanolamine wherein these structures are further substituted by aliphatic organic acids having different carbon chain lengths, e.g. palmitoyl (16 carbons) and lauryl (12 carbons).

The term "non-phase transition liposome" refers to a liposome that does not display a phase transition temperature $T_C$ within a specified temperature range of interest. For example, if a liposome "A" has a phase transition temperature $T_C$ of 4° C., and the specified temperature range is from 10–50° C., then, over this temperature range, it is referred to as a nonphase transition liposome. In addition, since this particular temperature range is above the nominal $T_C$, liposome "A" will be in the fluid (liquid) phase state at all temperatures between 10° C. and 50° C.

The term "microinjection of liposomal drug" refers to the technique of using liposomes that are bound to a target cell surface, or that have been internalized by the target cell, to directly introduce drugs into the target cell. This technique is also referred to as "using liposomes as a cellular-level microsyringe".

THEORETICAL BASIS

Current methods of drug delivery via liposomes require that the liposome carrier will ultimately become permeable and release the encapsulated drug. This can be accomplished in a passive manner, wherein the liposome bilayer membrane degrades over time through the action of factors inherent in the body. Every liposome composition will have a characteristic half-life in the circulation or at other sites in the body.

In contrast to passive drug release, active drug release involves using an external agent or force to induce a permeability change in the liposome vesicle. Liposome membranes can be constructed so as to become destabilized when the environment becomes acidic near the liposome membrane (*Proc. Natl. Acad. Sci. USA* 84:7851 (1987); Biochem. 28:9508 (1989) and references therein). The liposome membrane can be chemically modified to provide an enzyme as a coating on the membrane which slowly destabilizes the liposome (*FASEB J*. 4:2544 (1990)). However, this technique is limited in that it does not allow modulation or alteration of drug release to achieve "on demand" drug delivery.

It has been recognized that a major barrier to the use of liposomes as drug carriers is the ability of the liposome to release the drugs on demand at the target sites (*Science*, 202:1290 (1978)). The specific use of applied heat to raise the liposome temperature to $T_C$ to make them permeable has been described (*Science*, 204:188 (1979)), and addressed in U.S. Pat. No. 5,190,761, in which a method of activating liposomes to release their encapsulated drugs in tissue utilizing microwave radiation is described.

A third method to achieve release of active drug is to employ a liposome having a predetermined phase transition temperature, $T_C$, at or above the temperature of the target tissue (see for example *Radiation Res*., 112:161 (1990) and references therein). These liposomes are designed to be employed at temperatures slightly below their phase transition temperature, $T_C$, (where they are naturally permeable) so that in the temperature range of healthy or normal tissue the liposome membrane is in the solid ($T<T_C$) stage. This means that healthy tissue temperatures will maintain the liposomes below $T_C$ so they will not become leaky. This mechanism for drug release is capable of "on demand" drug delivery, since these liposomes experience a greatly increased membrane permeability at $T_C$ and this effects drug release. To release drugs from such phase transition liposomes placed in the body requires the application of heat until $T_C$ is achieved. Such liposomes are made of highly purified phase transition temperature phospholipid material (either as a single component or multi-component mixtures).

"On demand" liposome release can also be obtained utilizing high voltage electrical fields similar to those found in electroporation/electropermeabilization. It has been shown (Mueller et al. (1983) and Chang et al. (1992)) that exposure to brief external high voltage fields in both solid and fluid liposomes will promote the formation of pores and, if the electrical field is high enough, effect rupture. These effects can occur either at normal body temperature or over a wide range of temperatures. The electrical fields causing electropermeabilization act to trigger drug delivery in two ways: (1) by destabilizing the liposome bilayer so that membrane fusion between the liposome and the target cellular structure occurs, thus facilitating the direct delivery of drug into the target cell; and (2) by triggering the release of drug in high concentrations from liposomes at the surface of the target cell so that the drugs are driven across the cell membrane by a concentration gradient. In either case, the direct cellular-level microinjection of drug into the target cell is achieved.

A further consideration of liposome-mediated delivery relates to the potential for controlling the direction and speed of movement of charged liposomes utilizing subthreshold iontophoretic fields which are applied from the elements of the electrode array. These liposomes will contain negative external charges which should cause them to migrate through the extracellular fluid space towards the positive pole of the iontophoretic field, thus allowing differential positioning of the liposomes in vivo. In this aspect of the invention, a central electrode element in conjunction with satellite electrodes will act as confining dipoles to limit the excursion of the electrical field outside the desired area. Utilization of this aspect of the invention will allow for increased concentrations of materials in certain areas of the target body site which may have poor blood distribution, compressed cytoarchitecture, etc., features well documented in tumors.

Electroporation/Electropermeabilization

The difficulty in transporting a normally nonpermeable active agent across a membrane can be overcome by utilizing transient high permeability states induced by transitory high voltage electrical fields. This transient high permeability state can be used to increase the transport flux of molecules which may be assisted by a driving force such as concentration difference or hydrostatic pressure. Electroporation is characterized by a transient high permeability state and a decrease in the electrical resistance of the tissue caused by brief exposure to an abnormally high trans-tissue potential. The decreased electrical resistance can be used as an effective means of monitoring electroporation effects. For example, short electroporation pulses (preferably $10^{-6}$ to $10^{-3}$ seconds) are applied. At a fixed pulse width, the resistance of the sample will remain unchanged as the voltage magnitude of the electroporation pulses is increased. Above a certain threshold, however, the resistance rapidly decreases, with higher voltage pulses further decreasing the tissue resistance. Following this, the trans-tissue resistance can gradually recover to its initial value. The range of transmembrane potentials associated with electroporation is from approximately 500 to 1500 mV. These values are much higher than the normal physiological resting potential (approximately 100 mV) and generally above the magnitude of transmembrane potentials known to result in membrane rupture (approximately 300 to 600 mV). Thus, the relatively short duration of the electroporation pulses used to induce electropermeabilization is a key aspect of this process. It has been shown that electroporation can be accomplished in multilayer tissues, including skin and underlying tissue (U.S. Pat. No. 5,019,034). Further, this reference discloses the transport of molecules across tissue by applying an electrical pulse in order to cause electroporation and utilizing a driving force to move molecules across the region. In the specification "driving force" is defined as including iontophoresis, pressure gradients and concentration gradients. The reference also discloses the temporary increase of the permeability of tissue by applying an electrical pulse of sufficient voltage and duration to a region of tissue to cause a "reversible electrical breakdown" in the electroporated region, wherein the region is used as a site of molecular transport.

Further, a patent to Hofmann (U.S. Pat. No. 5,318,514) details an apparatus for implanting macromolecules such as genes, DNA or pharmaceuticals into a preselected surface tissue region of a patient.

Generally, for cells, electroporation results in non-thermal, short term membrane changes, with all damage or death occurring only due to long term osmotic pressure differences, or other physicochemical imbalances. Cell lysis or cell fusion can occur for some pulse conditions which induce electroporation. During this process, the values and changes in values of the electrical impedance between any pair of electrodes, either during or after any pulse or pulse series, can be monitored to allow a determination of the occurrence of decreased electrical resistance for any tissue transport situation.

Acute electropermeabilization events will also cause short term reversible changes in the local conductivity and should be detectable by applying small electrical fields across adjacent electrodes to determine those areas which have been adequately treated versus those areas which may require additional electroporation pulses to induce electropermeabilization.

Electrode Placement

One further aspect of the present invention relates to a system utilizing the placement of a plurality of electrodes (desirably at least 7 and less than 15) within or surrounding a predetermined three-dimensional region in the body. This region can be, for example, a tumor or other similarly diseased area, or any region in which the application of the present invention is deemed desirable.

The basic design of one embodiment of the present electrode array includes a central reference electrode surrounded by six geometrically-oriented electrodes (Hexasphere™). These electrodes are designed to contain the electrical field within the "sphere" defined by the electrode placement at points in space equidistant from one to another. This design is considered to be advantageous in that the electrical fields produced can be oriented to travel primarily across a hemi-diameter of the preselected region, e.g. a tumor, and remain "confined" within the substance of the target body tissue.

This electrode array design may also include synthetic microcylinder structures which may be used for local delivery of materials into the extracellular space such as drugs, and hyper- or hypo-osmotic elements which will facilitate the distribution of the electrical field and thus enhance the electroporation process.

Another aspect of the invention relates to the "preconditioning" of the predetermined tissue location in order to maximize the effect of the electroporation pulses. This preconditioning phase will generally comprise sub-threshold constant or alternating electrical field stimulation, using alternating current electrical fields, RF, ELF fields, and the like. This treatment is designed to increase the stochastic probability of sites of increased permeability on cell membranes in the predetermined location in the body, following the electroporation pulses. This aspect of the invention can also utilize the delivery of electrically conductive material to the predefined body site.

A further aspect of this invention is the enhancement of distribution of the liposome encapsulated material utilizing iontophoretic field application across the electrode array in various combinations designed to allow uniform concentration or, in some cases, deliberate asymmetry in concentration at specified sites.

A further aspect of the invention involves the use of non-ionic surfactants or other similar recovery techniques to aid the closure of pores formed in target body site following electroporation pulses. This aspect of the invention will aid in retaining the material delivered via the invention into target cells.

A further aspect of the invention involves the directed migration of charged liposomes to certain areas of the target body site, as defined by the subthreshold iontophoretic fields applied utilizing the electrode array. The liposomes used in this aspect of the present invention will desirably contain negative charges on the outer surface, which should cause them to migrate towards the positive pole of the iontophoretic field, thus potentially allowing differential positioning of the liposomes in vivo. As a feature of this aspect of the invention, the central electrode element in conjunction with the satellite electrodes will act as confining dipoles to limit the excursion of the electrical field outside the desired area. This feature will allow for increasing the concentrations of the liposome-encapsulated materials in certain areas of the target body site which may have differential blood distribution, cytoarchitecture, etc.

Yet another aspect of this invention relates to the method of protecting healthy tissues, such as brain tissues, from the electroporation pulses delivered to the target body site. There is a decreased probability of a given electrical field effect causing electroporation at lower temperatures, i.e. less chance for membrane destabilization to occur. A process which creates differential temperatures within the body should increase the probability that electroporation events will occur in the areas with higher temperatures, and decrease the probability in areas which are cooled significantly below body temperature. This technique of cooling selected tissue, e.g. the brain (otherwise known as cerebroplegia) and target body site using hypothermic solution of low conductance liquid is generally performed as follows (described with reference to the brain):

I Cooled blood or other perfusion solutions are administered via carotid injection, rapidly cooling the brain or target body site to 10–20° C. This methodology is designed to minimize the metabolic activity of the brain and to protect the healthy tissue from the permeabilization effects of electroporation pulses, which have reduced effect at lower temperatures. Also, cerebroplegia permits brief disruption of cerebral blood flow without significant damage to the neural tissue.

II Immediately after the cooling period (1–2 minutes), the cerebral blood flow will be replaced by hypotonic or other low conductance solutions in order to diminish the intravascular conductance of subsequent electroporation pulses. Following this infusion, the cerebral perfusion is temporarily disrupted (for 10–20 seconds), during which time:

III The target body site will be differentially heated by subthreshold electroporation pulses using lower voltage electrical fields with increased duration;

IV Immediately following the heating of the target body site, electroporation pulses will be administered via the electrode array (10–20 seconds); A non-ionic surfactant or other pore closure recovery method will be employed via circulating this material through the cerebral circulation, with preferential site of activity being the target body site;

V A non-ionic surfactant or other pore closure recovery method will be employed via circulating this material through the cerebral circulation, with preferential site of activity being the target body site;

VI Cerebral blood flow will be re-established with gradual rise in temperature of healthy tissue recovering to normal; and VII The electrode system will be removed.

In certain aspects, the present invention involves the preparation of drugs encapsulated in liposomes affected by electroporation pulses using very brief high voltage electrical fields. The permeability of liposome membranes depends on many factors which include their lipid composition, the type of drug, drug sequestration into the bilayer membrane or into the aqueous interior compartment, the site of release and other complex physicochemical properties. It is generally recognized that undisturbed liposomes are not very permeable, but can be made so by altering membrane properties.

Thus, the invention provides a novel method of placing a series of electrodes into the target body site of interest, thereby setting up geometrically-oriented electrical fields by which to perform electroporation. As an adjunct to the electroporation, liposomes encapsulating various compounds, and designed to maximize the effect of electroporation pulses and deliver drugs to diseased tissues are also utilized and methods are described to iontophoretically localize charged liposomes.

Additionally, a method is described which affords protection of normal tissue using thermal insulation via cerebroplegia techniques. This will allow normal tissue to establish a differentially lower temperature than the tumor or diseased tissue which is heated using subthreshold electroporation pulses, followed by electroporation pulses designed to both incorporate liposomes and release liposome contents into the extracellular fluid (ECF) for uptake into the electroporated cells.

The present invention desirably utilizes liposomes which possess a phase transition temperature $T_C$ within the temperature range of interest, generally several degrees below their transition ($T_C$) temperatures. Such liposomes are referred to as phase transition liposomes which will be in the fluid (liquid) phase state following application of electroporation pulses. Drug delivery using electrical fields using liposomes at temperatures corresponding to $T_C$ have been previously described in U.S. Pat. Nos. 4,801,459 and 5,190,761.

Lipid Components

The liposomes used in this present invention are small unilamellar vesicles (SUV). The liposomes are formed from standard vesicle forming lipids, which generally include neutral and negatively charged phospholipids with or without a sterol, such as cholesterol. The selection of lipids is generally guided by considerations of (a) desired liposome size and ease of liposome sizing, and (b) lipid and water soluble drug release rates from the site of liposome injection.

Typically, the major phospholipid (PL) components in the liposomes are phosphatidylcholine (PC), phosphatidylglycerol (PG), phosphatidylserine (PS) phosphatidylinositol (PI) or egg yolk lecithin (EYL). PC, PG, PS, and PI having a variety of acyl chain groups or varying chain length and degree of saturation are commercially available, or may be isolated or synthesized by well known techniques. The degree of saturation can be important since hydrogenated PL (HPL) components have greater "stiffness" than do unhydrogenated PL components; liposomes made with HPL components will be more rigid. In addition, less saturated PLs are more easily extruded, which can be a desirable property, particularly when the liposomes must be sized below about 0.3 microns, for purposes of filter sterilization or other formulation requirements. Methods used in sizing or filter-sterilizing liposomes are discussed below.

Protective Agent

It is well known that the lipid components of liposomes promote peroxidative and free radical reactions which cause progressive degradation of the liposomes. This problem has been discussed at length in the U.S. Pat. No. 4,797,285. Briefly, the patent discloses that lipid peroxidative and free radical damage effect both lipid and entrapped drug components in a liposome/drug composition. It is noted that the extent of free radical damage to lipid and drug components was reduced significantly when a lipophilic free radical quencher, such as alpha-tocopherol ($\alpha$-T) was included in the vesicle-forming lipids. A significantly greater reduction in lipid damage and drug modification was observed when the lipid/drug composition was formulated in the presence of both $\alpha$-T and a water soluble, iron-specific chelator, such as ferrioxamine. Since ferrioxamine can complex tightly to ferric iron at six coordination sites, it is likely that the compound acts by inhibiting iron-catalyzed peroxidation in the aqueous phase of the liposome suspension. The effectiveness of the two protective agents together suggests that both iron-catalyzed peroxidative reactions occurring in the aqueous phase, and free radical reactions being propagated in the lipid phase are important contributors to lipid peroxidative damage.

Lipophilic free radical scavengers can be used in the composition employed herein and include the preferable α-T, an analog or ester thereof (such as alpha-tocopherol succinate), butylated hydroxytoluene (BHT), propyl gallate, and their pharmacologically acceptable salts and analogs. Additional lipophilic free radical quenchers which are acceptable for parenteral administration in humans, at an effective level in liposomes, may be used. The free radical quencher is typically included in the lipid components used in preparing the liposomes, according to conventional procedures. Preferred concentrations of the protective compound are between about 0.2 and 2 mole percent of the total lipid components making up the liposomes; however higher levels of the protective compound, particularly α-T or its succinate analog, are compatible with liposome stability and are pharmacologically acceptable.

Liposome Formation

The liposome suspension of the invention can be prepared by any of the standard methods for preparing and sizing liposomes. These include hydration of lipid films, solvent injection, reverse-phase evaporation and other techniques such as those detailed in Am. Rev. Biophys. Bioeng., 9:467 (1980). Reverse-phase evaporation vesicles (REVs) can be prepared by the reverse-evaporation method as described in U.S. Pat. No. 4,235,871, incorporated herein by this reference. The preparation of multilamellar vesicles (MLVs) by thin-film of a lipid or by an injection technique is described in U.S. Pat. No. 4,737,923, incorporated herein by this reference. In known procedures which are generally preferred, a mixture of liposome forming lipids dissolved in a suitable solvent is evaporated in a vessel to form a thin film, which is covered by an aqueous buffer solution. The lipid film hydrated to formation MLVs, typically with sizes between about 0.1 to 10 microns.

Either the REVs or MLVs preparations can be further treated to produce a suspension of smaller, relatively homogeneous-size liposomes, in a 0.1 to 1.0 micron size range. One effective sizing technique involves extruding an aqueous suspension of the liposomes through a polycarbonate membrane having a selected uniform pore size, typically 0.2, 0.4, 0.6, 0.8 or 1 micron as shown in Ann Rev. Biophys. Bioeng., 9:467 (1980). The pore size of the membrane corresponds roughly to the largest sizes of liposomes produced by extrusion through that membrane, particularly where the preparation is extruded two or more times through the same membrane.

A more recent technique involves extrusion through an asymmetric ceramic filter, as detailed in U.S. Pat. No. 4,737,323, incorporated herein by this reference.

Alternatively, the REVs or MLVs preparations can be treated to produce small unilamellar vesicles (SUVs). Among the advantages of smaller, more homogeneous-sized liposomes are, for example, the higher density of liposome packing at a mucosal surface, the higher likelihood of intact liposomal incorporation into the electroporated cells, and the higher concentration of liposome encapsulated drug transported to the target organ. Because of the small particle sizes, SUVs in suspension can be distributed in the minute capillary bed of the central nervous system.

One preferred method for producing SUVs is by homogenizing an MLV preparation, using a conventional high pressure homogenizer of the type used commercially for milk homogenization. Here the MLV preparation is cycled through the homogenizer with periodic sampling of particle sizes to determine when the MLVs have been substantially converted to SUVs.

The larger liposome vesicles, whether MLVs or LUVs, however, have other advantages such as, for example, a larger capacity for drug encapsulation and may therefore be preferred for certain routes of administration or delivery to specific targets, in particular target body site outside the central nervous system.

The use of all SUVs, LUVs, MLVs, OLVs, or mixtures thereof, is contemplated to be within the scope of this invention depending on intended therapeutic application and route of administration.

A selected drug is encapsulated in the liposomes by using for example the procedure described in U.S. Pat. No. 4,752,425, incorporated herein by this reference.

These vesicles can preferably be made by reverse phase evaporation using chloroform and isopropyl ether. However, the vesicles prepared in this or any other suitable manner, and for reasons which become more apparent later, may optionally contain to radioisotope markers as described in U.S. Pat. No. 5,190,761 and incorporated by reference herein. Additionally, these liposomes can contain various boronated compounds, among them BSH, BPA, boronated porphyrins etc. These compounds are useful in following the release and quantification of release of liposomes in brain areas which are subsequently analyzed by inductively coupled plasma-atomic emission spectroscopy (ICP-AES).

Liposome Sizing and Sterilization

Following liposome preparation, the liposomes may be graded to achieve a desired size range and relatively narrow distribution of liposome sizes. A preferred size range is about 30–100 nm. Several techniques are available for obtaining liposomes of a desired size. Sonicating a MLV liposome suspension either by bath or probe sonication produces a progressive size reduction down to SUVs less than about 0.5 microns in size. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both techniques, the particle size distribution can be monitored by conventional laser beam particle size discrimination.

The filter sterilization method can be carried out on a high through-put basis only if the liposomes have been first sized down to less than or equal to the 0.2–0.4 microns range. The importance of sterilization for any pharmaceutical product is well understood and it will be appreciated by using this filtration sizing step the sterilization will also be achieved at the same time and without additional steps.

Removing Free Drug

The initial liposome suspension may contain up to 50% or more drug in free (non-encapsulated) form. The drug can be encapsulated such that it is sequestered in the liposome bilayer (lipophilic compounds) or entrained in the liposome internal aqueous region (hydrophilic compounds). The presence of such free drug may in some cases be tolerated but in many other cases is undesirable because these drugs are often toxic in their free state. Therefore, in order to maximize the advantages of liposome-encapsulated drug and to minimize the effect of the free drug, it may be important to remove free drug from the final injectable suspension.

Several techniques are available for removing non-entrapped compound from a liposome suspension. In one technique, the liposomes in the suspension are pelleted by high-speed centrifugation, leaving free compound and very small liposomes in the supernatant. This approach is followed where several liposome washings are employed. Another method involves concentrating the suspension by ultrafiltration, then resuspending the concentrated liposomes in a drug-free replacement medium. Alternatively, gel-filtration can be used to separate liposome particles from the solute molecules.

Following treatment to remove free drug, the liposome suspension is brought to a desired concentration for administration. Typically, the liposomes are administered by i.v., i.m., or s.c. injection. Thus, the liposome may be resuspended in a suitable volume of injection medium such as saline, or other pharmaceutically acceptable injectable medium as may be appropriate for the drug suspension or route of administration. The resuspension is particularly appropriate where the liposomes have been concentrated, for example by centrifugation or ultra-filtration, or concentrating the suspension volume. The suspension is then sterilized by filtration as described above. These media and other representative injectable components are well known and set forth in Remington's Pharmaceutical Sciences, 17th Ed., Mack Publishing, Easton, Pa. 1985.

Non-Phase Transition Liposomes

Liposomes without a reverse transition over a specified temperature range can be prepared when a suitable perturbing agent is added to the phospholipid membrane, or when a multicomponent phospholipid liposome is constructed. Thus, for example, the perturbing agent cholesterol can be added to the membrane of a liposome displaying a $T_C$ over a specified temperature range of interest. Such a membrane is comprised of, for example, a single highly purified phospholipid. At sufficient concentrations, cholesterol converts this material essentially into a nonphase transition liposome. The obliteration of a reverse transition will render liposome membranes impermeant and highly stable with regard to leakage of drug. In the method here described using electrical fields as a triggering agent for liposome drug release, one observes a significant increase in drug release from nonphase transition liposomes during treatment with electrical fields.

The use of non-phase transition liposomes as drug delivery vehicles has several advantages. First, these liposomes are extremely stable with respect to temperature since they do not exhibit a phase transition temperature, $T_c$, at which they become permeable. Of some benefit is the fact that they can be prepared with very inexpensive materials, since the use of highly purified phospholipid is not required. Using liposomes as drug delivery vehicles, via this technique, has additional advantages. Liposomes of this type can be prepared to include a broad range of drugs which may then be usefully administered and/or released to specific cells, organs or tissue, either intermittently or over a sustained period of time. Non-phase transition liposomes allow the administration of relatively high drug doses of relatively toxic drugs with reduced side effects that are usually associated with free drug at such high concentrations.

Delivery of Liposomes

There are three main routes by which materials will be delivered to, e.g., the interstitial spaces of internal tumor areas: (1) local delivery by injection; (2) intravascular administration combined with electropermeabilization of selected areas of the vasculature to increase the unloading of materials to the interstitial fluid; (3) utilization of liposome-encapsulated materials to penetrate tumor tissue via the localized disruption of the blood-brain barrier caused by the tumor. These liposomes would be allowed to cross the blood-brain barrier and accumulate in interstitial space of the tumor. The liposomes would carry either cytotoxic materials or hyperconductive compounds to be distributed by convection or by convection/diffusion processes in combination with pressure gradients.

Local injections would be carried out by utilizing either iontophoretic or simple mechanical injection of specific volumes of materials designed for cell killing or compounds designed to aid electrical field propagation within the tumor. Delivery would be accomplished employing a microtubular system which would be incorporated within the implanted electrode array. Compounds would be infused slowly and allowed to move away from the injection site(s) either by normal convection or diffusion.

The second method involves the vascular (intra-arterial or intravenous) administration of compounds which would be carried to the cerebral intravascular spaces, followed by electropermeabilization pulses which would be delivered to the selected cerebral vessels. It is expected that this would enhance the extravasation of compounds from those already leaky capillaries into the interstitial spaces. This would be of particular benefit in those tumor types which do not significantly alter the intact blood-brain barrier.

Liposomes may be administered to persons as a liposome depot at a tissue site or may be administered directly into the circulation. Circulating nonphase transition liposomes will not release the drug unless subjected to an electrical field. In turn, electrical fields may be selectively directed only to target areas where the drug release is desired. All other liposomes outside the target area will not release the drug; liposomes in the general circulation and liposomes at a distant liposome depot outside of the exposure site will remain intact until their eventual sequestration by the reticuloendothelial system in the body. The process of drug release using electrical fields may be repeated intermittently until all drug is released from the liposome population.

Driving Forces

In order for the released drugs to effectively penetrate the cells, it is recognized that some force must move molecules across the regions of the tissue undergoing electroporation. The driving force may be electrical, such as iontophoresis, or it may be another physical or chemical force such as provided by a temperature gradient, a pressure gradient, or a concentration gradient. Additionally, the driving force may comprise acoustic or optical pressure.

Once the compounds have been delivered within tumoral tissue, it is preferable to evenly distribute the compounds throughout the interstitial compartment, either for purposes of cell killing or for purposes of evenly distributing conducting ions for later electroporation work. There are several natural phenomenon which mediate distribution as well as several supplementary methods which might be used to either improve the area of distribution, the concentration of compounds in a given area or increase the speed of distribution. The optimal scenario in any therapeutic modality would be for each tumor cell to have equal access to the treating agent.

There is a sequential order to the delivery of most blood-borne molecules to tumor cells. Molecules must be delivered to the general region of the tumor cells via intravascular transport, then move across the microvascular walls to the interstitial spaces where they move through the interstitial matrix either via convection, diffusion to the tumor cells, or under the influence of externally applied gradients such as pressure gradients or electrical fields. The interstitial fluid environment in which these molecules move in tumors is quite different than normal tissue. Diffusion is proportional to the concentration gradient in the interstitium and convection is proportional to the pressure gradient in the interstitium. In most tumors, there is a significant heterogeneity in the perfusion within a given tumor, combining multiple zones of well-vascularized cells with semi-necrotic regions of intermediate perfusion and possibly one or more necrotic, avascular regions. In general, the wellpermeabilized regions have low interstitial pressures, leading to increased extravasation of fluid and macromolecules from the vasculature. These macromolecules extravasated in the outer zones of the tumors may then move towards the center by the slow diffusion processes. opposing this movement centrally is the movement of molecules by convection which moves in the direction of high to low pressure, thus centrally towards the periphery and into normal tissue (Jain (1987)).

In the case of a brain tumor, it is considered desirable that when electropermeabilization is performed, each tumor cell is porated and that all cells would have an adequate amount of the therapeutic agent outside of the cell (and thus able to enter the cell). The local and vascular delivery systems described above may not be able to deliver a uniform distribution of the agent, due to regional variations in blood supply, tumor density, necrotic zones, variations in interstitial space pressure, etc. It would thus be highly desirable to influence the distribution of such agents utilizing a variety of methods as described below.

Convection

From classical physiology, fluid movement across the endothelial wall is described by Starling's hypothesis:

$$j = \rho K(x)[(p_i - p_e) - (\pi_i - \pi_e)]$$

where
- K(x) is Starling's coefficient
- $p_i$=intraluminal hydrostatic pressure
- $p_e$=extraluminal hydrostatic pressure
- $\pi_i$=intraluminal osmotic pressure
- $\pi_e$=extraluminal osmotic pressure Starling's coefficient is a factor which includes the conductivity properties of the endothelial wall and other transport properties. In normal capillaries, it has been shown that the Starling's coefficient increases from the arteriolar to the venular side by as much as ten fold. A report by Peterson et al. (1973) has shown that the endothelial capillary wall in tumors has significantly greater permeable coefficients than normal vessels.

Darcy's Law describes the relationship between interstitial fluid velocity and an interstitial pressure gradient:

$$v_i = -K_t(P_e, x_i) \frac{\partial p_e}{\partial x_i}$$

where $K_t(P_e, x_i)$ is the Darcy coefficient and is a function of the interstitial pressure and properties of the medium. For general purposes, it is usually assumed to be a single property of the medium, such as porosity.

Convection describes material transport which occurs as a result of macroscopic movement of the volume element in which the material is found. There is a normal convective movement of interstitial fluid within the tissue compartments of both tumor and brain. It is clear from work by Jain and others that significant movement of interstitial fluid occurs from areas of high pressure, namely central tumor areas, to lower pressure areas in the periphery, resulting in a net outward movement of tumor interstitial fluid from the interior to the exterior. Therefore, one might exploit this movement by centrally injecting the desired compound and then relying on convection to move the materials. There are some problems with this approach however such as areas of differing pressure within the tumor and non-uniformity of the interstitial compartment within the tumor.

In general, the interstitial space in tumors is very large compared with that in host normal tissues (Peterson (1979)). The interstitial space of tumors is composed predominantly of a collagen and elastic fiber network. Interspersed within this cross-linked structure are the interstitial fluid and macromolecular constituents (polysaccharides) which form a hydrophilic gel. Whereas collagen and elastic impart structural integrity to a tissue, the polysaccharides (glycosaminoglycan and proteoglycans) are presumably responsible for the resistance to fluid and macromolecular motion in the interstitium. In several tumors studied to date, the collagen content of tumors is higher than that of normal host tissue. On the other hand, hyaluronate and proteoglycans are, in general, present in lower concentrations in several tumors studied to date than in normal host tissue. Therefore, the large interstitial space and low concentrations of polysaccharides suggest that values for interstitial hydraulic conductivity and diffusivity should be relatively high in tumors. Some experimental work supports this. Tumor transport coefficients with values an order of magnitude higher than those of several normal tissues should favor movement of macromolecules in the tumor interstitium.

Various experiments have attempted to quantity fluid movement in tumor and normal tissue. In other papers describing bulk movement of interstitial fluid., fluid loss has been measured at 0.14–0.22 ml/hr per gm of tissue in four different rat mammary carcinomas. This fluid leakage leads to a radially outward interstitial fluid velocity of 0.1–0.2 $\mu$m/sec at the periphery of a 1 cm 'tissue isolated' tumor. The radial outward velocity is an order of magnitude lower in a tumor grown in the subcutaneous tissue or muscle. A macromolecule at the tumor periphery has to overcome this outward convection to penetrate into the tumor by diffusion. The relative contribution of this mechanism of heterogeneous distribution of macromolecules in tumors is, however, smaller than the contribution of heterogeneous extravasation resulting from elevated pressure and necrosis. It is also apparent from experimental studies that large molecules move mainly by convection.

Diffusion

Diffusion is the movement of molecules from an area of high concentration to an area of lower concentration. Molecular diffusion results from the random motion of the molecules of the material and depends upon the molecular weight of the material, concentration gradient, and other factors. Diffusion of materials along concentration gradients is also well described in tumor and normal neural tissue and can be relied upon for some degree of distribution of materials which are injected in concentrated amounts. High molecular weight compounds have low diffusivity in brain or tumor and for low molecular weight compounds, capillary loss and metabolism often underlie the restricted distribution. Diffusion is unaffected by pressure gradients. Small molecules such as oxygen and conventional chemotherapeutic drugs which have MW lower than 2,000 daltons leave blood vessels and migrate through normal tissue mainly by diffusion.

The time required for a molecule with diffusion coefficient D to move by diffusion across distance L is approximately $L^2/4D$. For diffusion of IgG in tumors, this time is of the order of 0.5 hr for a distance of 100 $\mu$m, ≈2 days for a distance of 1 mm, and ≈7–8 months for a distance of 1 cm. Consider a hypothetical tumor that is uniformly perfused, has nearly zero interstitial pressure, and has exchange vessels ≈200 $\mu$m apart. In such a tumor, IgG would reach uniform concentration approximately 1hr post injection, provided the plasma concentration remains constant. In a normal tissue with the value of D lower by an order of magnitude, it would take ≈10 hours to reach uniform concentration. In a more realistic scenario, the tumor vessels are ≈200 μm apart and uniformly perfused, but the interstitial pressure in the center is increased such that fluid extravasation, and hence, convective transport of macromolecules across the vessels have stopped. In such as case, the only way macromolecules can extravasate in the center is by the slow process of diffusion across vessel walls. Also, they can reach the center from the periphery (where interstitial pressure is near zero) by interstitial diffusion. If the distance is 1 cm from center to periphery, it would take months to travel this distance. If, as a result of elevated interstitial pressure and cellular proliferation, the central vessels have collapsed completely, then there is no delivery of macromolecules by blood flow to the necrotic center. In such as case, there are no molecules available for extravasation by diffusion across a vessel wall, and consequently the central concentration would be even lower.

Mathematical modeling conducted by Jain's group (Jain (1994)) postulates that a continuously supplied monoclonal antibody of molecular weight 150,000 daltons could take several months to reach a uniform concentration in a tumor that measured 1 cm in radius and had no blood supply at its center.

Pressure Gradients

The enhancement of convective fluid movement utilizing small amounts of continuous pressure has been demonstrated by several studies, increasing flow by at least an order of magnitude. Bobo et al. (1994) explored the use of pressure gradients to enhance convection volume of distribution ($V_d$) of materials in cat brain. The $V_d$ of the infusion concentration increased linearly with the infusion volume. Immediately after the completion of infusion of 600 μl of solution, approximately 50% of the cat hemisphere had received ≧1% of the concentration of $^{111}$In-Tf in the infusion. Since the normal rate of diffusion of $^{111}$In-Tf over the three hours of infusion would be negligible, this distribution was felt to be the result of convection. The rates of infusion during the experiments proved significant, as infusion rates greater than a few microliters per minute produced leakage of the infusion solution out of the cannula tract and lowered the infusion pressure. The CNS is normally able to remove fluid from the interstitial space in edematous white matter at about 0.3–0.5 μl min$^{-1}$, equivalent to approximately 2.5 μl/min per hemisphere in the cat. Two hour infusions spread $^{111}$In-Tf ≈1.5 cm and sucrose ≈2.0 cm in an anterior-posterior direction immediately after completion of the infusion. Although predominantly distribution in white matter immediately after infusion, $^{111}$In-Tf showed increasing penetration of gray matter over the next 24 hours. Sucrose was extensively distributed into gray matter by two hours. In these experiments, the infusion of $^{111}$In-Tf solutions occurred at concentrations that were nearly five orders of magnitude greater than the reported tissue-averaged density of receptors, thus avoiding the problem of $^{111}$In-Tf binding to receptors and being internalized by cells.

With regards to the side effects of infusion, all of the interstitial brain infusions of the study were well tolerated and were not associated with any hemodynamic instability during the infusions. Two chronic animals demonstrated transient lethargy and weakness that resolved within 24 hr. Structural studies by Marmaroue et al. have demonstrated that myelinated axons remained spatially related via oligodendroglial processes despite the expansion of the extracellular space and there was orderly reconstitution of the tissue as the edema resolved, leaving only a mild fibrillary astrocytosis. In a variety of models, cerebral edema does not cause neurologic dysfunction as long as intracranial pressure does not appreciably elevate. Furthermore, evidence suggests that even when edema is severe enough to cause neurologic dysfunction, deficits related to edema are reversible. Thus, evidence suggests that cerebral edema per se does not alter brain function as long as there are no associated herniations of cerebral tissue, significant elevation of intracranial pressure, or reduction of cerebral blood flow below the normal range.

Therefore, the possibility exists of utilizing pressure gradients within extravascular space of tumors, which is significantly increased above normal tissue, to allow spread of materials over 1.5–2.0 cm of the interstitial compartment from each electrode/injection sites.

Positioning of the Electrical Field

It is logical to begin consideration of the application of an electrical field to a biological tissue by considering the site of origination of the electrical field to be applied. In reviewing the pertinent literature regarding in vivo brain electroporation or electropermeabilization, only bipolar electrode configurations have been used to "bridge" across the tissue to be electropermeated. In recent work by Ceberg et al. (1994), the results demonstrated that the electropermeabilization effect in brain tissue extended well beyond the expected and desired confines of the theoretical electrical field lines. Both electrode sites were located outside of the primary tumor tissue, potentially allowing for significant current flow into adjacent normal tissue.

In order to provide equal distribution of electropermeabilization voltages, electroporation pulses should ideally be distributed in uniform fashion throughout the target body site, minimizing the flow of current in retrograde fashion up the electrode tract. Subsequent refinements in the electrode design may provide for a facilitation of closure of the brain tissue around the electrode as it penetrates the brain, thus creating a natural barrier to the flow of current. Additionally, secondarily coating the surface of the electrode would also aid in creating a resistance to retrograde current flow, as would the use of appropriate dielectric insulators. Additional measures for prevention of electrode tract flow include physical barriers such as collars or balloon devices which would fit around the shaft of the electrodes.

The electrodes will be placed by two methods: (1) stereotaxic placement or (2) direct placement. Prior to therapy all tumor patients undergo at least one form of routine imaging study (MRI or CT) to localize and differentiate diseased from healthy tissue. Recent advanced imaging techniques combine these techniques with stereotaxic coordinate systems which enable the precise localization of target body sites within three-dimensional space. In addition, valuable information may be gained as to the detailed internal architecture of the tumor such as variations in tumor density and vascular supply. This information should prove useful in directing the strength and number of electroporation pulses which in turn determine the magnitude of the electropermeabilization field within different regions of the tumor. By pursuing this rationale, it should prove beneficial to permeabilize areas of the tumor, such as the central necrotic region, which are inherently more resistant to the electroporation pulses effects.

The first placement method involves utilization of stereotaxic imaging information to precisely locate the electrodes both within and around a tumoral or diseased area of the brain. The general method would be similar to other methods described in the literature which involve delivery of the electrodes to their desired location utilizing either hand-held instrumentation or mechanical drive systems which are linked to the three-dimensional imaging coordinates. It is anticipated that for the purposes of the acute implementation, electrode immobilization provided by normal frictional forces would be adequate and not require positional stabilization.

The second method involves the use of hand-held or guided instrumentation during surgical biopsy procedures. In this procedure, electrode insertion would be verified by intraoperative radiological methods and although potentially less accurate, would nonetheless may be more widely utilized as dictated by efforts toward cost effectiveness.

Iontophoretic Fields

There are a number of aspects of the invention which will utilize iontophoretic or electrophoretic fields. The first involves enhancement of distribution of the hyperconductive materials which will be moved throughout the interstitial compartment via constant or alternating field application. Low intensity electrical fields (Chang et al. (1992)) have been proven useful for electroporation and also useful for cell fusion. The application of low-intensity AC field has resulted in a dielectrophoretic process resulting in the formation of pearl chains. This low intensity field results in alignment and positioning of cells such that their membranes are perpendicular to the electrical fields where conditions for fusion are most suitable. Also related is the fact that AC fields are also particularly important when fusing enucleated oocytes to cells with reduced diameters since the polarization caused by the AC field will aid in bringing their membranes into contact.

A further aspect involves the "preconditioning" of the target tissue (utilizing sub-threshold DC, AC, RF, or ELF electrical fields) in order to maximize the effect of the electroporation pulses. This treatment is designed to increase the stochastic occurrence of increased permeability sites in cell membranes of the target body site. This aspect of the invention may also rely upon the delivery of electrically conductive material to the target body site as defined above.

Use of Electrical Fields To Trigger Drug Release

The present invention is typically used in the following manner: A suspension of liposomes with encapsulated drug is prepared in sterile pharmaceutical formation suitable for i.v., i.m., s.c., or any other route of injection administration.

The suspension is then administered to the patient in need of treatment and the liposomes are subsequently treated with a safe but effective dose of electrical field. "Safe" in this context means that it does not heat the tissue to hyperthermic (43° C.) or supra-hyperthermic (>43° C.) temperature levels that may cause tissue damage.

The liposomes may be injected as localized depots or may be injected to circulate freely in the blood stream with the potential to be targeted to specific tissue sites and localize at a site of interest. The latter case is termed targeted drug delivery and the bound liposomes are treated with the electrical field to trigger localized drug release at the target site.

The electrical fields causing electroporation act to trigger drug delivery in two ways: (1) by destabilizing the liposome bilayer so that membrane fusion between the liposome and the target cellular structure occurs, thus facilitating the direct delivery of drug into the target cell; and (2) by triggering the release of drug in high concentrations from liposomes at the surface of the target cell so that the drugs are driven across the cell membrane by a concentration gradient upon via the created electropores. In either case, the direct cellular-level microinjection of drug into the target cell is achieved.

The electrical field source is then placed, desirably via the HexasphereTM electrode array, into the tissue of desired localization of the drug delivery. Although the liposomes are delivered systemically, with some exception, the localized field effect serves to constrain the electroporation effect to the geometrically-oriented area as defined by the electrodes. Thus, the liposomes in this area are treated and will release encapsulated drug as they circulate through this local electrical field. The patient can be treated with the field for a single treatment or be treated at different time periods (i.e. multiple doses) using a number of intermittent applications of the field.

The specific process of targeted drug delivery using liposomes via the present method has several unique advantages. The liposomes affinity for the target cell results in adsorption or binding to the target cell resulting in an extraordinarily high concentration of encapsulated drug at the surface of the target cell. A typical target cell has a diameter of approximately 7 $\mu$m (7,000 $\mu$m). This is large compared to the size of a liposome vesicle (having a typical diameter of 100 nm). Approximately 450 million liposome vesicles can be bound to the surface of such a target cell, and each liposome vesicle can be loaded with drug at a high concentration (>100 mM). This situation represents the most effective means for bringing high concentrations of drug to the surface of a target cell. Using electrical fields via the method provided, the problem of releasing drug from these bound liposomes can be overcome.

Method of In Vivo Electroporation

Electroporation is a phenomenon in which the membrane of a cell exposed to high-intensity electrical field pulses can be temporarily destabilized in specific regions of the cell. During the destabilized period, the cell membrane is highly permeable to exogenous molecules present in the surrounding interstitial or extracellular spaces.

The phenomenon of electroporation has been described as a threshold dependent phenomenon, in that the threshold field strength ($E_C$) for electroporation is a "point of no return". If the electric field E ($\geq E_C$) is maintained, the electropores induced by the supercritical field increase in number and size until, at a supercritical number density and pore size, the membrane ruptures. If electroporation pulses of short duration $\Delta t$ are applied, the field is already switched off before rupture can occur. It is therefore appropriate to view membrane electroporation as being characterized by critical values for the extent ($\xi$) of structural rearrangement, for the field strength ($E_C$), and for the pulse duration ($\Delta t_C$). The primary requirement for the onset of electroporation is that the threshold $\xi_c$ has to be reached. The minimum field strength to attain the critical value $\xi_C$ is the critical field strength $E_C$. Once the threshold $\xi_C$ is reached (E$\geq E_C$), the actual electroporation starts and proceeds unidirectionally until the rupture threshold $\xi_r$ is attained, i.e. where the membrane ruptures. If the field is reduced below $E_C$ or switched off before $\xi_r$ is reached, the pores reseal such that the original membrane state appears to be completely restored. Since the threshold $\xi_C$ is attained faster at a higher field strength, the minimum pulse duration $\Delta t_C$ that is required for the onset of the electroporation process decreases as the applied external field increases.

Sudden non-thermal rupture (irreversible mechanical breakdown) occurs in bilayer membranes exposed to a transmembrane potential, U, in the approximate range 200 $\leq U \leq$ 500 mV for a relatively long time (i.e., $\Delta t \geq 10^{-4}$ sec). Larger but shorter duration U results in non-damaging, more rapid discharge of the membrane. Typical square wave pulse characteristics which cause electroporation are a pulse width in the range of from $10^{-7}$ to $10^{-4}$ sec, and amplitudes at the membrane in the range of 500 to 1500 mV.

A recent paper by Prausnitz et al. (1994) noted that the actual electrical field in electroporation may be up to 10% less than the nominal electrical field, perhaps due to voltage drops at the electrode interface. Therefore, although only nominal electrical fields are generally reported in the literature, differences between nominal and actual electrical fields are probably present in many electroporation protocols.

The recovery process in cells versus artificial bilayers is much slower and strongly temperature dependent in cells. It has also been reported that: (1) The greater the applied field strength, the larger the probe molecules which can permeate into the treated cells preceding cell lysis; (2) The longer the pulsed electric field, the larger the probe molecules can permeate; (3) Pulsed electric field treatment in a higher-ionic-strength medium (e.g. saline, leads to creation of small pores, and in a lower-ionic-strength medium, e.g., isotonic sucrose, to bigger pores when identical pulsed electric fields were used; and (4) Pulsed electric field treatment at higher temperatures leads to a lower critical voltage, implying that the induced pores could be larger (Kinosita et al. (1977)).

However, Prausnitz et al. (1994) noted that longer pulses were less effective than multiple pulses for maximizing transport while minimizing damage. Furthermore, multiple pulsing enhanced uptake strongly at lower electrical field strengths, but weakly at higher field strengths. This suggests the existence of a transport maximum beyond which additional pulses can not increase uptake. It follows that more pulses at moderate E lead to the same uptake as fewer pulses at higher E. However, pulses at larger E are generally associated with lower cell viability (Chang et al. (1992)). Multiple pulses at moderate E may maximize transport and cell viability. Further work demonstrated a comparison of the effects of multiple pulses and single pulses having the same time integral of electrical field strength (INT) where INT is defined by $$INT = \int_0^\infty E_0 e^{-t/\tau} dt = E_0 \tau$$

where
  $E_o$ is the peak field strength,
  t is time, and
  $\tau$ is the decay time constant. D1573713
For multiple pulses, $$INT = \Sigma E_o \tau$$

The flux of molecular transport through a tissue is a function of the product of the tissue permeability, the driving force and the area of the tissue. Two mechanisms of electroporation-mediated permeability are utilized in the present invention:

(1) transient electropores: Within a few msec after the cessation of the electrical field, these pores partially decrease in diameter and adopt a stable configuration. The pores allow translocation of various molecules (influx of exogenous molecules and efflux of cytosolic compounds) by two slightly different mechanisms. Large molecules and even macromolecules are assumed to cross only the transient electropores. They must be present in the extracellular medium during the electroporation pulses and efficient electroporation requires long electroporation pulses or a large number of pulses and an E generally greater than the absolute or $E_C$. The amount of compound electroincorporated is inversely related to the molecular weight.

(2) long-lasting electropores: Created after shorter electroporation pulses, these electropores are only efficient for ions and small or intermediate size molecules. It is possible to add the exogenous molecules to the electroporation cells after electrical field delivery as well as before. Concentrations on both sides of the plasma membrane are roughly equilibrated.

With respect to resealing, the higher the temperature, the more rapid the resealing. There is about one order of magnitude between 37° C. and 20° C., and another between 20° C. and 4° C. Also, the larger the electropores formed, the longer the time necessary to recover the initial membrane impermeability. Resealing appears to be also a function on ionic strength, osmotic pressure, the presence of membrane perturbing agents and integrity of the cytoskeleton.

It has been shown (Andreason et al. (1989)) that electroporation using a single high voltage square wave pulse was not effective for gene treatment. However, following this pulse with a series of low voltage pulses allowed gene transfer to occur and yielded significantly greater efficiency of transfection. Electroporation using the same series of low voltage pulses without the initial high voltage pulse did not result in detectable electroporation. Additionally, the viability of cells following electroporation appears to be greater than that observed with exponentially decaying waves. The effectiveness of complex series of pulses suggests that the mechanism of electroporation may depend on the exact characteristics of the electroporation pulses, rather than simply membrane effects.

The cells of a tissue are connected to each other, in particular through gap-junctions, establishing an electric continuum which results in a great difference as to what happens when an electrical field is applied on a cell suspension. Some studies (Maurel et al. (1989)) showed that monolayer threshold of electroporation was lower than suspension cells of the same type.

The work of Kinosita et al. (1977) and Rols et al. (1992) suggests that the electroporation phenomenon can be described as a three step process of: (i) induction of transient permeated structures for electrical field intensities greater than a threshold value $E_C$; (ii) expansion of these permeated structures which is related to the slope dP/dE of the permeabilization curve; and (iii) resealing of the electropores.

Resealing of field-induced membrane perturbations is a prerequisite for entrapment of membrane impermeable substances, and the restorative kinetics are highly dependent on temperature. At physiological temperatures, the resealing is very rapid (few minutes). At low temperatures (4–10° C.), resealing is very slow. Resealing properties also depend on $\Delta t$ and $E_C$. To overcome the nonuniform permeability pattern in the membrane, it is important to apply several consecutive pulses. Time interval on the order of 1–2 seconds to allow sufficient time to reseal the lipid bilayer structure of the biological membrane.

The procedures involved in using electroporation via the Hexasphere™ electrode array revolve around placing the array such that the electrical fields produced are oriented such that they travel across the hemi-diameter of the tumor or diseased area and remain confined within the substance of the target body site. Concomitant with this is the need to electrically isolate each electrode with respect to one another in order to drive the electroporation pulses "through" tissue rather than permit retrograde transmission back up along the electrode tracts. The electrodes will be spaced using stereotaxic equipment, with the core electrode(s) placed within the tumor or diseased material. Following this, the remaining electrodes will be placed into satellite positions, for example as illustrated in FIG. [?]. Techniques to insure proper placements of the satellite and core electrodes will involve imaging studies performed prior to the procedure, or else via direct operative placement at the time of biopsy or debulking procedures. The electrodes will typically be placed with the aid of a stereotactic instrument through burr holes in the skull, drilled down to the dura mater. Due to the anatomic difficulty in approaching the inferior surface of a predetermined area in the brain, the Hexasphere™ electrode array will desirably be oriented such that the inferior most electrode points will be placed at 45° angles with respect to the coronal plane using the vertical meridian as reference.

At this point, the tumor will have threshold electroporation pulses applied, likely in an alternating fashion utilizing different electrode sites in order to allow for complete distribution of current density to all parts of the tumor. As the electropermeabilized or electroporated cells spill the cytoplasmic contents, the conductivity will significantly increase, allowing subsequent pulses even greater effect on the cell population. The specific sequencing of the pulses may prove important in allowing complete coverage of the tumoral area. Following placement of the electrodes and subsequent to the preconditioning phase of the procedure, electroporation pulses (8–12) can be delivered using standard electroporation units (e.g. Instrument Research Co.). These pulses will consist of rapid serial square-waved pulses of approximately 400–1300 V/cm, with pulse duration of ranging from 10 μsec to 1 msec delivered at one pulse per second. The intensity of the electrical pulses will be checked by a digital storage oscilloscope connected to the electric pulse generator. This set of stimulus parameters has been experimentally used by Ceberg et al. (1994) as well as Salford et al. (1993) and in human clinical trials. The initial sequence of electroporation pulses may be followed by a second or even third series of pulses, dependent upon conditions.

The occurrence of electroporation effect can be detected by monitoring the tissue for a decrease in electrical resistance, which, along with an enhanced tissue permeability, is the characteristic effect of electroporation. Therefore, some measure of the effectiveness of the electroporation pulses may be appreciated by measuring the relative conductance between electroporation electrodes following the treatment pulses. In other words, prior to the first series, a series of smaller brief pulses can be delivered between electrodes in serial fashion to determine the pre treatment conductance. Following the treatment pulses, follow-up measurements may help determine the success of the electroporation pulses by documenting the presence of an increased conductance due to large ionic shifts as a result of the poration.

There are a number of technical issues which must be considered when contemplating electroporation of a tissue as a whole, rather than tissues in suspension or culture. The overall effectiveness of electroporation is dependent upon the spread of the electrical field through the tissue and the voltage potential each cell membrane sees. Sources of heterogeneous electroporation within a cell population include:

cell size, shape and orientation non-uniformity of electrical field cell-cell separation tissue heterogeneity (perturbation of local field by tissue)

membrane composition (varies within cell population)

Because of the above mentioned properties, it is useful to consider other methodologies to insure the uniformity of the applied electrical fields throughout the target body site tissue.

Use of Cerebroplegia

The use of intermittent hypothermic cerebral perfusion (cerebroplegia) has been reported in the literature as a concomitant procedure to surgeries involving intracardiac repair in infants, aortic arch replacement, chronic pulmonary embolectomy, and selected neurosurgical and vascular surgical procedures. In general, these procedures have involved cooling the entire body using cardiopulmonary bypass procedures in which the subjects have been maintained at low core hypothermic conditions (<20° C.) over 1–2 hours. Cerebroplegia is aimed at cooling the brain only through selective perfusion of the brachiocephalic arteries with cool blood or fluids (6–12° C.) (analogous to cold blood cardioplegia).

The perfusion equipment utilized include basically a heat exchanger which allows blood derived from the general circulation (or perfusion fluid) to be cooled to 6° to 12° C. A perfusion line distributes the perfusate to the brachiocephalic arteries and special cannulae are available in several diameters to perfuse the carotid arteries.

Perfusion solutions will likely consist of either cooled blood which has been slightly heparinized, or asanguineous oxygenated solution (NIH cardioplegic solution; Robbins et al. (1990)), consisting of 0.45 normal saline with 2.5% dextrose, mannitol, sodium bicarbonate, lidocaine, nitroglycerine and calcium chloride. This solution also has 300 ml of oxygen added to produce a $PO_2$>600 mm Hg (oxygen content=1.5 mmol/dl) at pH 8.0±0.1.

Additionally, several other hypotonic solutions, can be utilized for brief time periods to introduce minimally conductive solutions into the cerebral vasculature. The primary value of these solutions is to provide oxygen delivery to the tissues and clear metabolic by-products. Crystalloid has some obvious advantages such as simplicity of delivery. However, blood clearly provides superior buffering capacity and oxygen free radical scavenging properties and should generally be preferred.

The patient is then prepared and anesthetized, with continuous monitoring of electroencephalogram, rectal and nasal temperatures. The subjects will have T shunts placed in the carotid arteries bilaterally.

Thereafter, patient cooling is initiated. In small animals, this will consist of cooling (with cooling pads and ice packs to the periphery) down to nasopharyngeal temperature of 12–15° C. In large animal subjects and humans, this will consist primarily of cardiopulmonary bypass with cooling to 20° C. When proper core temperatures are achieved, both carotid arteries are cannulated and held by means of pursestring sutures. The proximal limb of the carotid shunt will be occluded with the delivery of solution into the distal carotid artery through the side port of the shunt. The proximal limb is then opened to establish cerebral reperfusion at the conclusion of the period.

It has been shown that the administration of cerebroplegia solution maintained ATP and CrP at significantly higher levels and Pi at a lower concentration, for all points during the cerebroplegia period. It has also been demonstrated that cerebroplegia produces significantly higher values of intracellular pH throughout the arrest periods.

The cold perfusion solution is then initiated and maintained until the electroencephalogram demonstrates total disappearance of activity (generally 3–16 minutes in humans). After this time (flat electroencephalogram) the cerebroplegia will be converted from a continuous flow to an intermittent flow. The pressure in the carotid arteries will be maintained to approximately 30–40 mm Hg, which approximates normal arterial pressures in the rodent population, versus 60–70 mm Hg in humans.

After the appropriate procedures have been performed, the carotid solution is gradually rewarmed and then bypass is discontinued. The cannulae are removed carefully to prevent the introduction of air bubbles.

Of additional benefit is the use of selective calcium antagonists and prostaglandin derivatives as protective agents during the hypothermic ischemia periods.

The small amount of oxygen delivered to the brain at reduced temperatures and corresponding reduced metabolic demands is sufficient for the maintenance of high-energy phosphates. Also, the intermittent delivery of an alkalotic solution could neutralize and washout ischemic metabolic by-products, resulting in a less acidotic cellular environment.

Strategy to Seal Cell Membranes Post Electroporation

A further aspect of this invention involves the use of recovery agents such as non-ionic surfactant or other similar agents to aid the closure of pores, electropores or cell membrane defects formed in target body site following electroporation pulses. This technique will aid in retaining the material delivered via the liposomes into target cells.

Biological lipid membranes are supermolecular assemblies of biological surfactants that spontaneous aggregate in an aqueous environment. During an ultrastructural examination of electroporated cell membranes, Chang and others (Chang et al. (1992)) demonstrated that stable structural defects occur in cell membranes. Their studies demonstrated pore diameters in the range of 100 nm. It is theoretically possible for a surfactant molecule to fill a 100 nm diameter defect in the cell membrane. The physics of membrane formation are such that it is favorable for surfactants to formation sheets across such defects. Therefore, it appears that the problem of restoring integrity to a damaged cell membrane is equivalent to the problem of achieving a high enough concentration of the correct surfactant at the site of damage. These compounds must not be toxic. Work by Lee et al. (1992) has found that one such surfactant (Poloxamer 188) was able to seal electropermeabilized skeletal muscle fiber cell membranes by placing it into the solution in which the cell was contained. This material is a reverse tri-block copolymer that has hydrophilic ends and a 'hydrophobic' center. It is known to adhere to cell membranes. In vivo administration of this compound into the circulation of a rat demonstrated successful repair of electroporation damaged muscle tissue membrane in an island flap model. This was reported to be the first direct demonstration of membrane repair in vivo. An adequate supply of surfactant molecule present in the extracellular spaces, by incorporating the surfactant material into liposomes which are preloaded into the electroporation treatment area, should prove beneficial in obtaining the desired result. The material has also been demonstrated to perform successfully within a 30 minute period of time.

Another well established membrane recovery technique in electroporation has been well studied and is related to the temperature at which the post electroporation membrane resides. By cooling the membrane, the permeabilization effect persists much longer as compared to permeabilization found at increasing temperatures. Therefore, manipulation of the rate at which the post cerebroplegia brain is rewarmed will influence the duration of the electropermeabilization effect and the resealing rate of the cell membrane.

"Pre-conditioning" for Electroporation Effects

Another aspect of this invention is enhancement of the conductance of the electrical field throughout the target body site utilizing liposome-encapsulated particular materials designed to allow application of similar electrical fields throughout the target body site as defined by the electrode array. Local delivery of electrically conductive solutions (e.g. ionic solutions, Fe++-containing solutions, etc.) designed to facilitate the spread of the electrical field throughout the interstitial spaces of the tissue defined by the outline of the array would assist in preconditioning the predefined region and create a more uniform field conductance, thus maximizing the electroporation effect.

This aspect of the invention will involve the use of subthreshold electroporation pulses which will be used to influence the distribution of free ions throughout tumor interstitial fluids.

There are a number of factors which suggest that sub-threshold electrical field application may influence the overall electroporation treatment pulses. First, even very small field intensities may cause electroporation, provided the field application is long enough. Second, if a second electroporation pulse hits the membrane patch which resides, not in the closed membrane state, but in a partial electropore state, the change induced by the second pulse is facilitated, because the pore transitions have already been facilitated by the first pulse. Third, the existence of transient aqueous pores can be consistent with the known behavior of bilayer membranes at low E. Fourth, low intensity electrical fields (Chang et al. (1992) page 320) have been proven useful for electroporation and also useful for cell fusion. The application of low-intensity AC field has resulted in a dielectrophoretic process resulting in the formation of pearl chains. This low intensity field results in alignment and positioning of cells such that their membranes are perpendicular to the electrical fields where conditions for fusion are most suitable. Also related is the fact that AC fields are also particularly important when fusing enucleated oocytes to cells with reduced diameters since the polarization caused by the AC field will aid in bringing their membranes into contact. The energy needed to form an aqueous pore is reduced as the transmembrane voltage is increased by application of an external electrical field (Weaver (1993) page 428) which raises the possibility that the pre-conditioning effects may in fact consist of one large electroporation pulse followed by a series of smaller pulses (Weaver (1993) pp. 429–430)). Further support for this notion stems from the fact that the signature of electroporation is a tremendous increase in electrical conduction which is measured and is believed to be due to ionic conduction through transient aqueous pores.

During the application of a subthreshold ($E<E_C$) electrical field, there are a number of subcritical membrane changes which occur, namely from $\xi_o$ to $\xi_C$, which represent reversible structural rearrangements such as the increase in number and size of hydrophobic defect sites and micropores in the bilayer. The minimum field strength to attain the critical value $\xi_C$ is the critical field strength $E_C$. Once the threshold $\xi_C$ is reached ($E \geq E_C$), electroporation starts. In fact, the data suggests that interfacial polarization precedes the structural transitions (Neumann (1987)). It is further elaborated by Neumann (at page 82) that the return to the closed membrane state M after switching off the field occurs in the absence of the external field. Given the sequence $$M \Rightarrow (P_{HO})_r \Rightarrow (P_{HO})r_c \Rightarrow (P_{HI})r_c \Rightarrow \ldots P_{CR}$$

where sequence of membrane changes from the poreless state M to hydrophobic ($P_{HO}$) to hydrophilic ($P_{HI}$) pores, the return transition $P_{HO} \Rightarrow P_{HI}$ (involving reorientation of the wall lipids) may face major activation barriers. Thus, if now a second pulse hits the membrane patch in the $P_{HI}$ state, the change induced by the second pulse is facilitated, because the transitions $P_{HO} \Rightarrow P_{HI}$ have already been caused by the first pulse.

Pre-conditioning also describes an alteration of the interstitial fluid milieu in order to enhance the electroporation given a particular value of $E_C$. Therefore, conductivity of the electroporation pulse and its relationship to ionic interfacial polarization is necessarily considered. For low conductivity membranes of thickness d of cells of radius a, the stationary value is given by $$\Delta\phi(E) = -1.5 f(\lambda) aE | \cos \delta |$$

where $\delta$ is the angle between the membrane site considered and the direction of E. The conductivity factor $f(\lambda)$ is a function of the specific conductances or conductivities of the external solution ($\lambda_0 \geq 10^{-4}$ S cm$^{-1}$), of the cell interior ($\lambda_i \approx 10^{-2}$ S cm$^{-1}$), and of the membrane ($\lambda_m \approx 10^{-7}$ S cm$^{-1}$), respectively and of the ratio d/a.

Usually, $\lambda_m << \lambda_i$, $\lambda_0$ and d<<a such that $$f(\lambda) = [1 + \lambda_m (2 + \lambda_i/\lambda_0)/(2 \lambda_i d/a)]^{-1}$$

From this, it is readily seen that an increase in the external ionic strength leading to an increase in $\lambda_0$ will increase $\Delta\phi$. This is consistent with the notion that the interfacial polarization is associated with ion accumulations at the interfaces of the membrane. Therefore, efforts to increase the $\lambda_0$ of the interstitial fluids will increase the effect of the electroporation pulses, thus allowing either more electroporation at a given value of $E_C$ or else the same effect at decreasing levels of $E_C$. The present invention proposes to deliver liposomes with hypertonic materials within them to the tumoral or diseased sites; then at subthreshold values of $E_C$, effect release of the materials which will diffuse into the interstitial medium and cause a relative increase in $\lambda_0$. Then, during the electroporation phase, more effective electroporation will result, causing increased number of cells to undergo electropermeabilization and thus be susceptible to the liposomes containing the drug compound to be delivered.

Thus, the present invention includes the delivery of materials which will aid in the pulse conduction through the interstitial compartment. This may be accomplished utilizing liposomes or may involve the already described local delivery methods of injection followed by distribution utilizing electrical field influence upon charged particles. Alternatively, this increase in ionic strength in the interstitial fluid might be accomplished by first using liposome-mediated delivery of hypertonic materials to the tumoral or diseased sites; then at subthreshold values of $E_C$, bring about the release of the materials which will diffuse into the interstitial medium and cause a relative increase in $\lambda_0$. Thus, during the electroporation phase, a more effective pulse propagation will result, resulting in an increased number of cells which undergo reverse electrical breakdown.

One method to accomplish this would be the serial application of a low voltage field across all elements of the array. The range of voltages would be 10 to 100 V. Consideration is also given to the possible utilization of an AC field which may be phase shifted in order to provide some asymmetry of the field duration, thus pulling ionic elements in one direction. The duration of the pulses will most likely be in the 0.5–5 second range. Multiple pulses will be required with some interval between each pulse ranging from 500 msec to 5 sec. It is anticipated that it will take on the order of minutes but less than 2 hours to accomplish the pre-conditioning. This estimate is based on diffusion studies which indicate this order of magnitude of time.

The application of the subthreshold electroporation pulses will desirably be computer driven and allow variation of the appropriate signal strength and duration, and also the number and order of active electrodes which will participate in each pulse. Furthermore, as suggested by Chang in U.S. Pat. No. 5,304,486, the fields (both AC and pulsed RF) may be generated by synthesizing the required electrical wave with a digital computer and amplifying the waveform using a power amplifier. It is anticipated that emphasis may be placed on those electrodes which will effectively concentrate or orient an electrical field in those areas which are deemed to require increased distribution of the facilitory ions due to increased density or decreased blood supply. The exact specifications of intensity of voltage, duration of pulses, number and orientation of pulses will be more fully elucidated as subsequent data are accumulated.

Another aspect of the preconditioning phase will be the use of a single electroporation pulse followed by a series of smaller subthreshold pulses.

This would involve the inclusion of liposomes filled with hyperconductive solutions used to preposition ionic compounds into the tumoral areas via the microcirculation and leaky capillaries. Once these are in place, a single electroporation pulse large enough to cause rupture of the liposomes would facilitate the selective delivery of hypertonic medium directly to the site of the target body site, thus enabling local specificity. As examples, hypertonic saline might be encapsulated in liposomes and delivered to the target body site via leaky capillaries. At this point, a single preconditioning electroporation pulse would be delivered which would rupture the liposomes, thus releasing contents into the extravascular (interstitial) spaces. Once this has been accomplished, then the preconditioning pulses would be used to effect migration of ionic elements throughout the interstitial fluid as described above.

Iontophoretic Field Application

Iontophoresis involves the application of an electromotive force to drive or repel oppositely charged ions through tissue. Positively charged ions are driven into the tissue at the anode while the negatively charged ions are driven into the tissue at the cathode. Therefore, at least two electrodes are used. One electrode, called the active or donor electrode, is the electrode from which the ionic substance is delivered into the body by iontophoresis. The other electrode, called the counter or return electrode, serves to close the electrical circuit through the body. If the ionic substance to be delivered into the body is positively charged, i.e. a cation, then the anode will be the active electrode and the cathode will serve to complete the circuit. If the ionic substance to be delivered is negatively charged (i.e. an anion), then the cathode will be the active electrode and the anode will be the counter electrode. Alternatively, the anode and the cathode may be used to deliver drugs of opposite charge into the body. Iontophoretic devices have been known since the early 1900's. U.S. Pat. Nos. 3,991,755, 4,141,359, 4,398,545, and 4,250,878 disclose examples of iontophoretic devices and some applications thereof.

Iontophoretic delivery devices can also be used to deliver an uncharged drug or agent into the body. This is accomplished by a process called electroosmosis which is the transdermal flux of a liquid solvent (e.g. the liquid solvent containing the uncharged drug) induced by the presence of an electrical field imposed across tissue by the donor electrode. Furthermore, iontophoretic devices generally require a reservoir or source of the agent to be delivered.

This aspect of the invention relates generally to the electrokinetic mass transfer of charged molecules or liposomes to particular regions of tissue based upon the desired overall interstitial fluid distribution. It is considered desirable to have an effective way of delivering the desired compounds without risking harm to the tissue structure from direct electrical contact and to avoid exposure of healthy tissue from the effect of the iontophoretic field. Care must be taken to avoid current flow along the path of least resistance into an area of tissue weakness, resulting in a localized burn. This pattern of current flow is also known as tunneling. Current carried through the liquid reverse (interstitial fluid) is carried by ions (ionic conduction). In order for current to flow, it is necessary for electrical charge to be transferred to chemical species in solution by means of oxidation and reduction charge transfer reactions at the electrode surfaces. The Nernst-Planck equation describes the movement of ionic species in mass transport. The first term describes the flux due to passive diffusion, which is proportional to the concentration gradient of species i. The second term describes the flux due to the electromigration or electrodiffusion, where the driving force is the gradient of electrical potential. The third term describes the flux due to convection, where the mechanism of transport is the movement of material by bulk fluid flow which is determined by the magnitude and direction of the bulk fluid velocity vector:

$$J_i = -D_i \Delta C_i - z_i F u_i C_i \nabla \Phi + C_i v$$

where
- $J_i$=flux of species i (moles/cm$^2$-sec)
- $D_i$=diffusion coefficient of i (cm$^2$/sec)
- $\nabla$=the gradient operator
- $C_i$=concentration of species i
- $z_i$=number of charges per molecule of species i
- F=Faraday's constant (96,500 coulombs/mole of charge)
- $u_i$=mobility of species i (velocity/force)
- $\Phi$=electrical potential (volts)
- v=velocity vector It is the sum of the fluxes resulting from these three processes, passive diffusion, electromigration and bulk fluid flow resulting from electroosmosis, which define electrotransport. Electroosmosis is defined as the volume flow of solvent through a charged membrane when an electrical field is imposed across that membrane.

In this device, the core and satellite electrodes will be used as iontophoretic devices with application of low voltage constant electrical fields across varying configurations in order to thoroughly distribute the various charged particles (including charged liposomes and other macromolecules including concentration ionic solutions for the improvement of intratumoral conductivity) throughout the tumoral or diseased tissue. DC currents in the micro to milliampere range will be utilized and the likely source of the constant current would likely be an appropriate field effect transistor and a variable resistor. These controllers are commercially available and normally consume only about 0.5–0.7 V. It is likely that there will be hindrance to high molecular weight compounds in the brain extracellular microenvironment Given a contiguous interstitial compartment it is reasonable to argue that either constant or pulsed electrical fields could be used to induce the migration of particulates to a given direction, thus allowing control of the distribution of ionic or otherwise designated materials which are locally injected. Thus materials would be "pulled" or "pushed" from one area of the tumor to the next, to introduce a desired pattern of uniformity or concentration.

Alternatively, the use of iontophoretic or pulsed fields can be employed to influence the migration of charged liposomes within interstitial fluid, again concentrating materials in particular locations. It has been demonstrated that constant electrical fields can increase the adsorption of liposomes to cell walls, thus increasing the likelihood of incorporation or of fusion following electroporation pulses. Also of use in this regard would be the utilization of phase transition temperature-specific liposomes for the purpose of controlled release at the appropriate temperature.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); mM (millimolar); $\mu$M (micromolar); N (Normal); mol (moles); mmol (millimoles); $\mu$mol (micromoles); nmol (nanomoles); kg (kilograms); gm (grams); mg (milligrams); $\mu$g (micrograms); ng (nanograms); L (liters); dl (deciliters); ml (milliliters); $\mu$l (microliters); vol (volumes); V (volts); mV (millivolts); cm (centimeters); mm (millimeters); $\mu$m (micrometers or microns); nm (nanometers); hr (hours); sec (seconds); msec (milliseconds); $\mu$sec (microseconds); and ° C. (degrees Centigrade).

Example 1

Brain Tumor Therapy

Brain tumors present a unique challenge to provide methods to selectively destroy tumor cells while preserving normal brain tissue.

There are a number of features which distinguish tumor from healthy tissue. It should be recognized that tumors are often unique from one another, even in the same subclass of cell type and that two tumors of the same type, age and size may have quite different internal structure and composition.

In spite of the differences between tumor cells, there are a number of generalizations which can be made to describe significant distinctions between tumor and normal cells:

1. The work of Peterson et al. (1973) has shown that the endothelial wall in tumors is significantly more permeable than normal vessels.
2. The extravascular compartment and the interstitial space are much larger in tumors than in normal tissues (Peterson (1979)). A recent article by Jain (1994) states that tumor cells often occupy less than half the volume of a tumor, with blood vessels comprising 1–10% of the volume and the extracellular matrix, a collagen-rich environment, occupying the remainder.
3. Vascular compression might occur followed by the development of central necroses. When the blood flow has stopped, the capillary endothelial cells die rapidly.
4. The extravascular space in human gliomas and meningiomas showed a large extracellular space: 20–40% in gliomas and 13–15% in meningiomas (Bakay, (1970); Rauen et al. (1967); Peterson et al. (1979)), while that in normal brain tissue was 6–7%.
5. The vascular volume in tumors seems to remain rather stable during growth. However, central necroses develop during growth after human brain tumors have reached a certain diameter (1–3 cm). This central necrosis is probably due to compression of vessels by increasing tumor cell masses or to a more rapid growth of tumor cell mass versus vascular endothelial cell proliferation. Tannock (1970) demonstrated a difference in the turnover times between endothelial (50–60 hours) and neoplastic cells (22 hours). Additionally, hypoxia, anoxia, and glucose depletion in the growing tumor caused by the absence of a sufficient neovascularization and general rarefaction of the terminal vascular bed might explain the development of necrotic areas in large tumors.

6. Morphological studies of blood vessels in human brain tumors showed fenestration, widened intercellular junctions, increased pinocytotic vesicles and infolding of the luminal surface, all of which suggest an increase in the transvascular transport of different materials. Most experimental data confirm a high permeability of the tumor capillary wall for large protein molecules. This is probably explained by morphological changes in tumor vessels as observed. It is also evident that the transport of large molecules across the tumor capillary wall is based on a passive diffusion, and concentrations of active drugs sufficient for a therapeutic effect are difficult to achieve. Normal passage of molecules across the blood vessel walls takes place across or between endothelial cells which line the vessel walls in a single layer. Molecules leave the vessels by either diffusion or convection except for cells such as white blood cells which leave the blood vessels by attaching to endothelial walls and deforming themselves to "squeeze through" the spaces between endothelial cells and thus gain access to the matrix. Once cells are in the interstitial matrix, they migrate by attaching to the matrix and crawling through it. This movement is influenced by the cells' adhesive properties and deformability. Certain molecules can facilitate or hamper cell motility and influence the direction of migration.

7. The vascular space of solid tumors becomes smaller as the tumor mass grows. In general, as the tumor increases in size, the vascular surface area decreases. The reduction of the vascular bed is accompanied by a widening of the vessel diameter (Vaupel et al. (1971); Vaupel (1974); Vogel (1965); Himas et al. (1974)), an increase in vessel length (Vaupel et al. (1971); Vaupel (1974); Jirtle et al. (1978)) and a broadening of the distance between tumor capillaries (Vaupel et al. (1971); Vaupel (1974); Vogel (1965)). In DS-carcinosarcoma, the mean intercapillary distance ranges are increased 3-fold during tumor growth from 3–12 gm. Also, the general rareification of the terminal vascular bed in DS-carcinosarcoma is accompanied by a 10-fold increase in the vascular flow resistance within the tissue when a tumor grows from 4–10 gm (Vaupel (1975)).

8. Tumor tissue exhibits a remarkable lack of homogeneity of blood vessel distribution and thus inhomogeneity in the supply of oxygen and nutrients to different parts of the tumor. This will certainly have an important effect on the manner in which materials are transported from the capillary to the tumor cell. This difference applies not only when comparing tumor center and peripheral areas, but also within neighboring parts of the superficial layers. Some regions of the superficial tumor may be absolutely ischemic (Vaupel (1977)). Regurgitation and intermittent circulation, i.e. periods of pre-stasis or stasis followed by resumption of blood flow sometimes in a direction opposite to the previous one are probably the 'normal' features of the intravascular transport system of neoplastic tissues. It is also estimated that in some tumor types, arterio-venous (AV) shunt perfusion represents up to 30% of the total perfusion.

9. There is also a pronounced tissue acidosis in tumor tissue which causes erythrocyte membranes to stiffen, reducing erythrocyte flexibility and fluidity and leading to a reduction of the microcirculation in malignant tumors. (Vaupel et al. (1976)).

10. Work in hyperthermia suggests that the preferential damage to tumor cells seen in this form of treatment may be mediated by differences in the tissue $O_2$ concentration of both tissues.

11. Due to the extreme tortuosity and number of vessels in the tumor, there is often a significant slowing of blood flow in the tumor which is accompanied by an abnormally high viscosity. The slowed flow often contributes to poor penetration of drugs such as chemotherapeutic agents. This may however, be turned into an advantage in that the accumulated drug which is trapped in this "reservoir" can slowly release drug gradually into neighboring regions of a tumor.

12. There is often an abnormally high pressure in the interstitial matrix which can slow the passage of large molecules across the vessel walls into the interstitial space. The pressure measurements also indicate that the pressure in tumor blood vessels is higher than it is in normal capillaries. It is believed that this elevation results mainly from the direct and indirect compression of the vessels by the proliferating tumor cells (Jain (1994)).

13. Gullino (1974) documented that approximately 10% of the blood fluid leaving a solid tumor oozes out from its periphery rather than draining via a vein. This oozing fluid migrates into the matrix of the normal cells carries drug molecules out and away from the tumor.

14. "The extent of liposome transport to the interstitium would be improved, however, if the permeability of nonleaky tumor vessels could somehow be increased." (Jain (1994)).

A. Brief Anatomy of Brain Tumors

This example is directed to the application of the present invention to malignant intracranial neoplasms, more specifically astrocytomas of which glioblastoma multiforme are a particularly lethal subclass. Gliomas constitute the majority of all primary brain tumors and occur more commonly in adults. There are three classes of astrocytomas: (low-grade) astrocytoma (LGA) which demonstrates mild hypercellularity and pleomorphism; anaplastic astrocytoma (AA) with moderate pleomorphism, increased proliferative activity and variable vascular proliferation; and glioblastoma multiforme (GBM) in which there is tumor necrosis.

Most astrocytomas are believed to begin as LGA, with potential evolution into AA and GBM as a result of dedifferentiation over time. Thus, regional heterogeneity is a finding of all the astrocytomas, leading to sampling errors and misdiagnosis. In this light, the current recommended technique for biopsy diagnosis is to sample stereotactic needle aspirates from one particular axis of the tumor so that representative samples are obtained from superficial, deep and central areas of the tumor.

The anatomy of these tumors may be characterized as diffusely infiltrating, expansile or as a combination of an expansile core and an infiltrating corona. The outer margins of the corona are usually poorly differentiated from normal tissue, making it difficult to separate out tumor from normal tissue in treatment settings. In some cases, this expansile tumor pushes normal tissue aside, showing a narrow rim of invasive cells which may form a cleavage plane for surgical resection. Low-grade astrocytomas tend to infiltrate diffusely and may not form a discrete mass. In contrast, AA and GBM form an expanding and infiltrating mass with a gradient of infiltrating cells extending away from the main mass. The primary pattern of spread is along the white matter tracts with generally less involvement of gray matter. Infiltrating tumor cells are usually accompanied by edema which may facilitate invasion. Individual cells may infiltrate a long distance from the main tumor mass and may produce secondary tumor masses. These multicentric astrocytomas can be tracked during autopsy proceedings quite often by following a trail of individual infiltrating cells. AA and GBM may also spread via seeding through the CSF with possible widespread subependymal and subarachnoid dissemination. To summarize, astrocytomas do not grow as spheres; instead their contours are highly irregular as their white matter extensions conform to the barriers of cortical convolutions and deep unclear structures.

One particular approach to this problem involves the sequential application of procedures which are designed to functionally isolate the target area of the brain while protecting normal neural tissue from treatment effects. Ultimately, specific measures are taken to "open" the cell membranes of the tumor cells, thus permitting entry of a desired therapeutic compound or agent which will be used to effect cell death.

Electrode Placement

The placement of electrodes within the predetermined area in the present invention is important to the overall success in achieving electroporation of the target region with maximal sparing of healthy tissue.

In the example of brain, integral to the placement strategy is the fact that the central electrode will be placed within the tumoral or diseased area in order to maximize the penetration of the target body site by the electrical field. It is considered desirable to ensure that the current flow is distributed in fairly uniform fashion throughout the target body site, and not allow for reflux of current in a retrograde manner along the electrode pathway which creates a disturbance in the blood-brain barrier. It is anticipated that appropriate design of the electrodes will facilitate closure of the tissue around the electrode, thus creating a natural barrier to the flow of current. Alternatively, coating substances on the surface of the electrode could aid in creating a resistance to current flow, as could the use of dielectric materials which could impede current flow. Also of use will be physical barriers, such as collar or balloon devices which would fit around the shaft of the electrode.

The electrodes will be placed by two methods: (1) stereotaxic placement or (2) direct placement. Prior to therapy, all patients will have some type of imaging study done to localize and characterize diseased tissue such as tumors within healthy tissue. Among the more advanced imaging techniques combine the imaging with stereotaxic coordinate systems which enable the precise localization of target body site within 3-D space. It is anticipated that such a coordinate system will be utilized in order to create a physical 3-D map of the tumor area, in addition to demonstrating internal variations in density, blood supply, etc. This information will be used to determine the best placement for the central electrode which will be placed in such a way as to allow access to the more dense areas of the tumor, thus insuring some flow of the electrical fields throughout the denser areas.

The second method would involve direct placement of the electrodes during surgical procedures, most likely resection or debulking procedures during which the electrodes would be placed in areas where the tumor either had been resected. Electrodes would consist of stainless steel, platinum, or platinum iridium electrodes which are coated with dielectric materials, for example Teflon.

Diagnostic Imaging Studies

Light Microscopy—A fairly uniform but nonspecific finding in tumors is the failure of local blood-brain barrier, which allows leakage of contrast material (contrast enhancement) into parenchymal tissues. Endothelial cells of cerebral capillaries have fused membranes, called tight junctions, which are the most important feature in regulating capillary permeability in the brain. The capillaries of normal brain are impermeable to intravascular injected contrast agents. Capillaries of tissues outside the nervous system are fenestrated with discontinuities in their basement membranes, with wide intercellular gaps permitting the passage of protein molecules from the lumen of the capillary into the extravascular space. The blood-brain barrier interfaces are not found in some regions of the brain. These areas include the choroid plexus, pituitary gland, cavernous sinus, pineal gland and dura. Capillaries in these areas are fenestrated and allow the diffusion of contrast material into the extracellular space and exhibit normal enhancement following the intravenous injection of contrast agents.

Tumors often stimulate the formation of capillaries in their tissue. Tumor capillaries in gliomas may have near-normal features with an intact blood-brain barrier. These areas of tumor will not enhance. In other more malignant gliomas, there is stimulation of capillaries the endothelia of which are fenestrated with poorly functioning or nonexistent blood-brain barrier. Metastatic brain lesions have non-CNS capillaries that are similar in to the tissue of origin, therefore possessing fenestrations and therefore enhancement under IV contrast conditions. This finding is also noted in other conditions such as infarction and infection. Highgrade tumors enhance owing to absence or deterioration of the blood-brain barrier, whereas well-differentiated tumors generally have intact blood-brain barrier and do not enhance. In general, these areas of enhancement are correlated well with a highly cellular and mitotically active neoplasm with proliferating vascular cells. Typically, a decreasing gradient of tumor cells extends away from the enhancing area into the surrounding edema. The majority of cells are within 2 cm of the original lesion. In GBM, it has been demonstrated that the microscopic infiltration of tumor was often over 2 cm from the enhancing rim.

Magnetic Resonance Imaging

The MRI is generally more sensitive to regions of edema than CT. The extent of T2-signal abnormality is currently the most accurate imaging study of the extension of tumor cell infiltration in primarily gliomas. Studies have demonstrated that tumor cells in high-grade astrocytomas are found even slightly beyond the region of high T2-signal intensity, thus beyond the areas defined by CT. An exception here is that gray matter or subarachnoid spread is not detected well by MRI. It is also clear that isolated tumor cells may infiltrate without eliciting edema, thus making them undetectable by MRI. The identification of these individual infiltrating tumor cells seems likely to remain beyond the range of detection by any radiological method.

Angiography

Angiography can demonstrate the vascular supply to a tumor and the positional relationship of the major intracerebral vessels, both arterial and venous, to the tumor mass. In many instances the angioarachitecture of the tumor may suggest the correct pathological diagnosis.

C. Surgical Treatment of Malignant Brain Neoplasms

Surgery is almost never the sole modality for treatment of malignant brain neoplasms but it is often combined with other treatment modalities within the context of a total treatment plan. It is now safely possible to remove the greater portion of glial tumors from virtually every location in the cerebral hemispheres as well as from many sites within the ventricles and in close proximity to the thalamus and basal ganglia. A radical excision of a glioma may be said to be the removal of its enhancing rim as well as the tissue defined by that boundary. However, this still leaves the scattered nest of malignant cells that extend for variable distances into the surrounding neuropil. Immediate benefits to surgical resection include: mechanical cytoreduction which produces a rapid cell kill, removes resistant cells and prolongs survival; amelioration of symptoms via improved neurological status and reduction of increased intracranial pressure; potentiation or facilitation of radiotherapy, chemotherapy and immunotherapy; and diagnostic precision with extensive tissue sampling, and tissue culture; improve the susceptibility of remaining cells by increasing access of drugs and biologicals to the remaining mass.

The mating of MRI/CT with traditional stereotactic frames to produce image-based stereotaxy is used to determine the three-dimensional coordinates of any point inside the head in relation to the stereotactic space delimited by the frame. These coordinates are used to control the entry of various micrometer driven instruments to any intracranial location. The patient is fitted initially with a CT and MRI-compatible stereotactic headframe (COMPASS system), which is applied under local anesthesia and mild sedation. This is secured to the skull by carbon fiber pins. These procedures are carried out under local anesthesia and employ small puncture holes in the skin along with twist-drill holes in the skull. Experimental techniques currently utilize such delivery methods for facilitation of entry of biopsy instruments, endoscopes, catheters for delivery of interstitial radiation or microwave hyperthermia, laser light for photoactivation chemotherapy, endoscopic laser ablation and catheter deposition of immunological reagents and other biologicals.

Another recently developed treatment modality employs stereotactic localization with focused beam ionizing radiation for the noninvasive destruction of small intracranial lesions. This technique, called radiosurgery, enables the neurosurgeon to deliver very intense radiation to a very sharply delineated area, thus destroying only the tumor and sparing the normal tissue. Instrumentation includes the Leksell Gamma Knife, cyclotron or synchrocyclotron instruments, modified linear accelerators.

D. Interstitial Radiation Therapy of Tumors

Brachytherapy (also known as interstitial radiation therapy) refers to treatment of tumors with radiation sources placed directly adjacent or into tumors. Advantages of this include the fact that the radiation emitted from a localized source implanted in tissue decreases rapidly with distance, owing to the inverse square law and to attenuation of the radiation as it passes through tissue. Additionally, low-dose-rate radiation tends to make proliferating tumor cells remain in $G_2$, a radiosensitive phase of the cell cycle during which RNA is synthesized prior to cell division. Normal, noncycling neuronal cells tent to remain in $G_1$, a radioresistant phase of the cell cycle. Another advantage of this therapy is that hypoxic cells (which might be found in the dense, central areas of a tumor mass) are less resistant to low-dose-rate radiation than to high-dose-rate radiation.

Tumors selected for implantation are supratentorial, unifocal, well-circumscribed lesions smaller than 5–6 cm in diameter. Patients undergo tumor resection 2–4 weeks prior to brachytherapy.

Brachytherapy has been combined with hyperthermic treatment immediately prior to the loading of $^{125}I$ and a second treatment after unloading the sources. The same catheters are used but the catheters are placed more peripherally, about 3–5 mm within the boundary of the contrast-enhancing tumor mass, evenly spaced about 1.2–2.0 cm apart from each other. In addition, one to three extra catheters are implanted for multipoint thermometry.

E. Chemotherapy

Chemotherapeutic agents are designed to affect the cell at the most vulnerable time in the cell cycle. These four stages are as follows: $G_1$ (protein synthesis); S (DNA replication); $G_2$ (RNA synthesis) and M (mitosis). Following these stages, cells such as neurons and glial cells are said to be post mitotic ($G_0$). As a general rule, chemotherapy agents are most effective during S phase and as most tumor cells are not in the S phase at any given time, only a portion of tumor cells are killed through the administration of a single cycle of chemotherapy. Therefore, agents are administered in multiple cycles to kill cells as they enter the correct cell cycle phase.

Chemotherapy relies on physical properties which exist in the tumor tissue which allow for penetration by these agents. The most effective chemotherapeutic agents for the CNS are highly lipid-soluble which allow relatively free access to the entire CNS and permit agents to reach not only the tumor mass, but also the malignant cells located at a distance from the main mass. The normal blood-brain barrier is created by tight cellular junctions and a lack of fenestrations of the brain capillary endothelial cells and basement membrane. Those non-ionized chemotherapeutic agents with high lipid solubility are able to cross the vascular barrier and enter the brain. Other chemicals may gain access to the brain by crossing vascular endothelial cells through nonspecific adsorptive transcytosis or receptor-mediated transcytosis. Some CNS areas have access to the intravascular compartment and include the pineal body, posterior pituitary, tuber cinereum, wall of the optic recess, area postrema, subfornical and commissural organs and the choroid plexus. Similarly, areas of the brain may allow breakdown of the normal blood-brain barrier due to trauma, vasculitis, radiation and infection in addition to infiltrating tumors.

Common modes of delivery include oral and intravenous routes. Intra-arterial treatment is an effective means of delivering high concentrations of chemotherapy directly to the region of interest while potentially reducing the risk of systemic toxicity. However, clinical trials have demonstrated multiple complications including depression of consciousness, paresis due to thromboembolic events, loss of visual acuity due to ocular toxicity, aphasia and white matter changes in the brain. Another delivery method for chemotherapeutic agents includes a synthetic wafer impregnated with a lipid-soluble N-(2-chloroethyl)-N-nitrosuoreas (CNUS) specifically known as Carmustine (BCNU). This wafer, which is placed on surgical resection sites, is formed utilizing a polyanhydride polymer and is designed to allow BCNU to slowly diffuse away from the polymer wafer into the interstitial compartment.

Intrathecal administration using cisternal or intraventricular injection (Ommaya reservoir) has been used to deliver larger molecular weight or polar drugs to tumor cells, bypassing the blood-brain barrier. However, drug penetration into the parenchymal tissue is often limited. For example, intrathecal administration of methotrexate penetrated to a depth of 3.2 mm at 1 hour. Drug distribution in the CSF is influenced by several factors, including bulk CSF flow, diffusion through the extracellular spaces of the brain and spinal cord, transport across the choroid plexus, removal by CSF absorption and diffusion from the extracellular space in the capillaries of the CNS. A related approach to maintain CSF drug levels would be to decrease CSF clearance. The normal mechanisms of drug clearance include CSF reabsorption, diffuse bulk CSF flow, transport across cell membranes, and absorption into capillaries. Probenecid, an inhibitor of the active transport of methotrexate, has been used clinically to prolong CSF levels of this drug, presumably by inhibiting the drug's active transport across the choroid plexus. Consideration has also been given to the use of acetazolamide to decrease CSF production, thereby reduce the bulk flow and turnover of CSF.

Intratumoral delivery methods have also been explored, primarily utilizing the Ommaya reservoir or an adapted tumor cyst device which permits direct installation of several chemotherapeutic agents into tumors. There are a number of technical limitations including the fact that water-soluble drugs are likely to diffuse slowly throughout the extracellular space. More lipid-soluble agents are likely to diffuse back across the barrier into the systemic circulation. Therefore, either of these limitations will require a large drug dose to overcome the diffusion problem. Harbaugh (1989) has described intratumoral chemotherapy through an external catheter infusion method. He also proposed the utilization of such devices for delivery of other therapeutic agents such as those which might be used in the treatment of Parkinson's or Alzheimer's disease.

Liposome mediated delivery has been used as a method of selective drug delivery and transport to tumor tissue. Early work has demonstrated the successful the incorporation of bleomycin and vincristine into liposomes of 0.1–15 μm diameter (Firth et al. (1984)). Experimentation in rats demonstrated a much slower release over time for the liposome delivered drugs versus "free" chemotherapeutic agents. MTX/cholesterol liposomes have been studied in primates and have demonstrated a higher average brain concentration than injection of free drug (Stewart (1984)). More recent research utilizing liposome-mediated delivery includes the work of Wowra et al. (1992); Gennuso et al. (1993); Fukuda et al. (1989); and Shibata et al. (1990).

Blood-brain barrier disruption chemotherapy has been attempted utilizing hyperosmolar iodinated contrast agents or compounds such as hyperosmolar mannitol, urea or arabinose to reversibly breach this barrier, temporarily opening the tight junctions and allowing transient unregulated entry of circulating substances into the CNS. A paper by Morantz et al. (1994) stated "When the use of lipid-soluble agents is not possible or if greater access to the brain parenchyma and tumor is desired, techniques of blood-brain barrier disruption are employed. This usually involves the intra-arterial infusion of mannitol . . . ", Neuwelt (see Morantz et al. (1994) pp. 776–777 for bibliography) has applied the observation to human and animal treatment. The state of the blood-brain barrier within any tumor is highly variable, even to within regions of a given tumor. There are several competing phenomenon which tend to rapidly reverse any advantage gained by partial or total breakdown of the blood-brain barrier in the region of the tumor. Given the fact that compounds diffuse from areas of high concentration to areas of low concentration, to the point of equilibrium. Therefore, even if a tumor has complete absence of a blood-brain barrier, because the barrier remains intact in the surrounding brain parenchyma, any immediate increased concentration of drug to the tumor rapidly diffused out to equilibrate with the remaining CNS (the "sink effect"). The technique of blood-brain barrier disruption provides an increased and more uniform drug delivery, decreases the tendency toward rapid diffusion and thereby allows tumor exposure to a higher concentration of drug for longer time period. However, this also exposes the normal CNS to a much higher concentration of chemotherapeutic agents.

The technique as detailed by Neuwelt involves opening the blood-brain barrier in the distribution of one circulation in the brain (carotid or vertebral artery). The exact distribution of disruption, therefore, is dependent on the flow, as determined by these vessels and the circle of Willis. One then selects the appropriate arterial distribution pertinent to tumor location. To obtain reversible disruption of the blood-brain barrier, a hyperosmolar saturated solution of 25% mannitol is injected at sufficient rate and volume to replace blood flow. This infusion must continue for approximately 30 seconds, at which time the threshold event of disruption occurs. Disruption is documented utilizing either Evans blue or the use of iodinated contrast agents and/or radioisotopes. The procedure is performed under general endotracheal anesthesia. Patients undergo retrograde catheterization of the femoral artery (Seldinger technique) and the selected artery is cannulated. Blood-brain barrier disruption allows for nonselective entry (for a period of approximately 30 minutes) of substances previously disallowed from the CNS and tumor. The use of blood-brain barrier disruption in cases of cerebral lymphoma have been most impressive given the often diffuse nature of this disease.

Photodynamic therapy involves exposure of a tumor to a photosensitizer such as a hematoporphyrin derivative (HpD) after which the tumor is exposed to light of an appropriate wave length to activate the sensitizer. This therapy relies on the selective tumor uptake of hematoporphyrin derivatives by the tumor compared to the surrounding normal brain. The HpD compound is infused preoperatively and at surgery the patient's tumor is exposed to light (630 nm) by an argon dye laser. The mechanism of cell necrosis may be related to activated free radicals, with damage to blood vessels and cell membranes. The mechanisms of HpD localization in tumor remain to be elicited. Uptake in various tumor types is variable, with glioblastomas demonstrating the highest uptake which was 30 times that in normal brain tissue. Low-grade tumors had a HpD uptake of 8 times normal tissue.

Boron neutron capture therapy is predicated on the preferential accumulation of boron ($^{10}B$) in conjunction with sufficiently high thermal neutron fluxes at the tumor site. The disintegration of the boron atom which is precipitated by collision with a slow neutron yields ionizing radiation of a very short diameter of travel, namely the approximate diameter of a cell. The slow neutron is several thousand times more likely to interact with a boron nucleus than with the nucleus of any element of human tissue. This therapy has been known and tried for many years with mixed results and has recently experienced a resurgence in it's popularity and research focus.

Drug rescue techniques are also employed in order to attempt to deliver high concentrations of cytotoxic drug to tumor and to increase the duration of tumor exposure to that drug. However, dose limitation is frequently due to extraneural side effects. The rescue technique might include administration of an antidote either concomitant with or sequentially to the administration of a chemotherapeutic drug. Other agents might be administered to protect certain areas of the body such as the use of mannitol to protect against nephrotoxicity or the use of systemic thiosulfate with cisplatin to protect against nephrotoxicity and reduce thrombocytopenia. Autologous bone marrow transplant has been used with BCNU and other drugs. Other attempts combine an "isolated perfusion" approach which uses an extraction hemoperfusion column or dialysis variation to remove the drug from the systemic toxicity. Similar novel approaches use the formation of antibody against a particular chemotherapeutic agent to bind and inactivate the drug. Such a method is particularly applicable to brain tumor treatment for which systemic toxicity is limiting, and systemically administered antibody can bind peripheral drug, yet has only limited access to CNS drug. Another application of monoclonal antibody (MAb) is the conjugation of the antibody to an enzyme to form a relatively high molecular weight molecule. The conjugate can be delivered across the blood-brain barrier with osmotic disruption where it binds to surface antigen and the barrier returns to a predisrupted condition. A low molecular weight prodrug capable of being activated to the cytotoxic agent by the antibody-bound enzymes is given, resulting in localized drug treatment.

F. Enhancement of Electrical Conductivity of Tumor

The internal architecture of a given tumor is thought to be highly variable, both within a given tumor and across the spectrum of other tumors of the same cytological origins. Therefore, the internal environment within the tumor is likely to be highly variable with respect to its ability to propagate electrical fields, and therefore equally variable with respect to the likelihood of electropermeabilization at any given site. In order to maximize the internal conductivity of the tumor, selective delivery and distribution of highly conductive materials throughout the interstitial space of the tumor, thus enhancing conductivity, is considered desirable.

G. Thermal Isolation of Tumor

Research indicates that there exists a direct correlation between temperature and the electropermeabilization threshold. There appears to be a direct positive effect on the likelihood of pore formation with increasing temperature. Conversely, decreasing the temperature at which electropermeabilization occurs results in a decreased likelihood of poration events at the membrane level. Therefore: (1) if a temperature gradient were to be established between normal and tumor tissue, with the tumoral tissue at a higher temperature than normal tissue: (2) if the electrical properties of both tissues were equal; then a simultaneous electrical field applied across both areas would result in a net increase in electroporation in the tumoral tissue. This differential electropermeabilization would increase as the temperature differential increased, although the linearity of such a relationship is yet to be established. Additionally, cooling the normal brain tissue would have significant protective effect both to the administration of other drugs or conductive materials as well as well as in the protection of normal brain tissue from the potential for seizure induction. The purpose of the cerebroplegia also extends beyond protection of the normal tissue by temporary interruption of the blood flow to the brain for periods of time for up to one hour. During this time either complete cessation of flow or intermittent pulsed flow can maintain the low metabolic requirements of the brain.

H. Heating of the Tumor

To create a temperature differential driving force as previously described, tumor tissue will be heated utilizing high voltage brief yet intense pulses. By increasing the duration of electroporation pulses, subthreshold poration fields can effect rapid heating of the intratumoral area, particularly as the rate of heating is a function of field strength.

It has been demonstrated that for high voltage fields, heating of $10^3$–$10^5$° C./sec can be reached. It is at this point that utilization of phase-transition-temperature liposomes results in the release of the contents of the liposomes as temperatures within tumoral tissue approach the critical threshold for liposome rupture within the interstitial space. This creates an "on demand" rupture of liposomes and distribution of their contents in the interstitial space adjacent to the cells which will be porated.

I. Blood Replacement by Hypoconductive Material

Once the cerebroplegia has been initiated, one can briefly replace the contents of the vascular tree with hypoconductive media. The vascular tree itself may provide a significant avenue of conduction of the electropermeabilization pulses, thereby carrying the electropermeabilization effect away from the tumoral area into the distribution of the normal brain tissue. It appears that replacing the vascular tree with hypoconductive medium would substantially eliminate the vascular tree as a likely conduit of the current, thereby confining the field to the predetermined region, namely the interstitial space. The feasibility of temporarily replacing the intravascular contents in the brain is based from work done in blood-brain barrier disruption studies which involve the injection of 25% mannitol solutions at a high rates of infusion, completely replacing the blood flow for up to 30 seconds. The key points of this technique include:

Hypothermia allows temporary interruption in the blood flow.

Lower temperature raises poration threshold in normal brain.

Hypotonic or hypoconductive medium in the vascular tree inhibits the spread of electroporation pulses via the vascular tree, thus directing the current into a higher resistance pathway, namely the interstitial space.

The injection of the hypoconductive medium will replace or wash out left over substances from the previous steps including liposomes, or other hyperconductive medium which might have remained in the vascular space.

A decrease in cerebral blood flow will enhance the effective arterial concentration in that slow blood flow allows higher tissue drug extraction.

All patent publications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the appended claims.

BIBLIOGRAPHY

Andreason, G. L. and G. A. Evans, *Anal. Biochem.* 180:269-275 (1989).

Bakay, L., *Brain* 93(4):693–698 (1970).

Bobo, R. H., D. W. Laske, A. Akbasak, P. F. Morrison, R. L. Dedrick, and F. H. Oldfield, *Proc. Natl. Acad. Sci. USA* 96(6):2076–2080 (1994).

Ceberg, C. P., A. Brun, L. M. Mir, B. R. R. Persson, and L. G. Galford. *Anti Cancer Drugs* 5:463–466 (1994).

Chang, D. C., B. M. Chassy, J. A. Saunders, and A. E. Sowers (editors), *Guide to ElectroPoration and Electrofusion*, Academic Press, Inc. New York (1992).

Firth, G. et al., *J. Neurology Neurosurg. Psychiatry* 47(6):585–589 (1984).

Gennuso, R. et al., *Cancer Invest.* 11(2):118–128 (1993).

Gullino, P. M. et al., *Cancer Res.*, 34(4):751–757 (1974).

Harbaugh, R. E., *Neurobio. Aging* 10(5):623–629 (1989).

Himas, D. E., and E. L. Gillette, *Cancer* 33(1):103–110 (1974).

Jain, R. K., *Cancer Res*. 47:3039–3051 (1987).
Jain, R. K., *Scientific American*, 58–65 (1994).
Jirtle, R. et al., *British J. Cancer* 37(6):1033–1038 (1978).
Kinosita, K. Jr. et al., *Nature* 268(5619):438–441 (1977).
Lee, R. C. et al., *Proc. Natl. Acad. Sci. USA* 89:4524–4528 (1992).
Maurel et al., *Experimental Cell Res*. 184(1):207–218 (1989).
Moranz, Robert A. and John W. Walsh (editors). *Brain Tumors, A Comprehensive Text*, M. Dekker, New York (1994) pg. 776–77.
Mueller, P., T. F. Chien and B. Rudy, *Biophysical J.* 44(3):375–381 (1983).
Neumann, E., A. E. Sowers, and C. A. Jordan, *Electroporation and Electrofusion in Cell Biology*, Plenum Press, New York (1982).
Neumann, R. et al., *Biochim. Biophys Acta* 898(3):338–348 (1987).
Peterson, H., *Tumor Blood Circulation Angiogenesis and Vascular Morphology: Experimental and Human Tumors*, CRC Press, Inc., Boca Raton, Florida (1979).
Prausnitz, M. R., C. D. Milano, J. A. Gimm, R. Langer and J. C. Weaver, Biophysical J. 66:1522–1530 (1994).
Rauen, H. M. et al., *Naturwissenschaften* 54(20):540 (1967).
Robbins, R. C. et al., *J. Thorac. Cardiovasc. Surg*. 99:878–884 (1990).
Rols, M-P and J. Teissie, *Biochim. Biophys. Acta*. 111:45–50 (1992).
Salfrod, L. G., B. R. R. Persson, A. Brun, C. P. Ceberg, P. C. Kongstad and L. M. Mir, *Biochem. Biophys. Res. Comm.*, 194(2):938–943 (1993).
Tannock, I. F., *Cancer Res.* 30(10):2470–2476 (1970).
Vaupel, P. et al., *Deutsche Medizinishce Wochenschrift* 101 (49):1810–1816 (1976).
Vaupel, P. et al., *Advances in Experimental Medicine and Biology* 94:367–375 (1977).
Vaupel, P. et al., *Experimentelle Chirugie* 156(4):283–294 (1971).
Vaupel, P. et al., *Microvascular Res*., 13(3):399–408 (1977).
Vaupel, P. et al., *Oncology* 30(6):475–484 (1974).
Vaupel, P., *Experientia* 31(5):587–589 (1975).
Weaver, J. C., *J. Cellular Biochem*., 51:426–435 (1993).
Wowra, B. et al., *J. Neuro-Oncology* 14(1):9–18 (1992).

We claim:

1. A system for the delivery of electroporation-inducing electrical fields to a patient comprising:

a plurality of electrodes adapted to be located within a predetermined three-dimensional space in a patient, said electrodes arranged to provide at least one reference electrode in electrically--conductive communication with at least two geometrically-oriented satellite electrodes; and electrical pulse generating means for generating electroporation-inducing electrical fields incorporating control means connected to at least three of said plurality of electrodes said control means capable of varying the number and order of electrodes that participate in each pulse delivered by said pulse generating means such that a pulse many be delivered to at least said reference electrode and at least two of said satellite electrodes simultaneously.

2. A system as recited in claim 1, said control means further comprising means to control the electrical parameters and temporal relationship of the electrical pulses applied to each of said electrodes.

3. A system as recited in claim 2, wherein said control means comprises a digital computer.

4. A system as recited in claim 2, wherein said control means can apply electrical pulses of different polarity to selected electrodes so as to redefine the reference and satellite relationship as between the plurality of electrodes.

5. A system as recited in claim 1, wherein the electrical pulse generating means generates an electrical field strength in the range of approximately 0.4 kV/cm to approximately 1.3 kV/cm in the tissue of a patient.

6. A system for the delivery of electroporation-inducing electrical fields to a patient comprising:

a plurality of electrodes adapted to be located within a predetermined three-dimensional space in a patient, said electrodes arranged to provide at least one reference electrode in electrically-conductive communication with at least two geometrically-oriented satellite electrodes;

electrical pulse generating means for generating electroporation-inducing electrical fields incorporating control means connected to at least three of said plurality of electrodes capable of varying the number and order of electrodes that participate in each pulse delivered such that a pulse may be delivered to at least said reference electrode and at least two of said satellite electrodes simultaneously; and control means connecting said electrical pulse generating means to at least three of said electrodes, which control means directs the electrical parameters and temporal relationship of the electrical pulses applied to each of said electrodes.

7. A system as recited in claim 6, wherein said control means comprises a digital computer.

8. A system as recited in claim 6, wherein said control means can apply electrical pulses of different polarity lo selected electrodes so as to redefine the reference and satellite relationship as between the plurality of electrodes.

9. A system as recited in claim 6, wherein the electrical pulse generating means generates an electrical field strength in the range of approximately 0.4 kV/cm to approximately 1.3 kV/cm in the issue of a patient.

10. A system for the delivery of electroporation-inducing electrical fields to a patient comprising:

a plurality of electrodes adapted to be located within a predetermined three-dimensional space in a patient, said electrodes arranged to provide at least one reference electrode in electrically-conductive communication with at least two geometrically-oriented satellite electrodes;

electrical pulse generating means for generating electroporation-inducing electrical fields incorporating control means connected to at least three of said plurality of electrodes capable of varying the number and order of electrodes that participate in each pulse delivered such that a pulse may be delivered to at least said reference electrode and at least two of said satellite electrodes simultaneously; and control means connecting said electrical pulse generating means to at least three of said electrodes, which control means can apply electrical pulses of different polarity to selected electrodes so as to redefine the reference and satellite relationship as between the plurality of electrodes.

11. A system as recited in claim 10, wherein said control means comprises a digital computer.

12. A system as recited in claim 10, wherein the electrical pulse generating means generates an electrical field strength in the range of approximately 0.4 kV/cm to approximately 1.3 kV/cm in the tissue of a patient.

* * * * *